United States Patent [19]
Fujio et al.

[11] Patent Number: 5,427,103
[45] Date of Patent: Jun. 27, 1995

[54] MRI APPARATUS FOR RECEIVING NUCLEAR-MAGNETIC RESONANCE SIGNALS OF A LIVING BODY

[75] Inventors: Koji Fujio, Tokyo; Masakazu Gotanda, Kanagawa; Tatsuya Yamaguchi, Tokyo; Shuichi Takayama, Tokyo; Takashi Tsukaya, Tokyo; Koichi Matsui, Tokyo; Hiroki Hibino, Tokyo; Keiichi Hiyama, Tokyo; Koichi Shimizu, Tokyo; Kenji Yoshino, Tokyo; Masaaki Hayashi, Tokyo, all of Japan

[73] Assignee: Olympus Optical Co., Ltd., Tokyo, Japan

[21] Appl. No.: 83,548

[22] Filed: Jun. 25, 1993

[30] Foreign Application Priority Data

Jun. 29, 1992 [JP] Japan ................. 4-171071
Jun. 29, 1992 [JP] Japan ................. 4-171134
Jun. 29, 1992 [JP] Japan ................. 4-171231
Mar. 16, 1993 [JP] Japan ................. 5-056133
Mar. 16, 1993 [JP] Japan ................. 5-056134
Mar. 16, 1993 [JP] Japan ................. 5-056135

[51] Int. Cl.$^6$ ............................. A61B 5/055
[52] U.S. Cl. ........................ 128/653.5; 128/4
[58] Field of Search .......... 128/653.2, 653.5, 656–658, 128/4, 6

[56] References Cited

U.S. PATENT DOCUMENTS

| 4,672,972 | 6/1987 | Berke | 128/653.5 |
| 5,035,231 | 7/1991 | Kubokawa et al. | |
| 5,036,464 | 7/1991 | Gillies et al. | 128/6 |
| 5,050,607 | 9/1991 | Bradley et al. | 128/653.5 |
| 5,170,789 | 12/1992 | Narayan et al. | 128/653.5 |
| 5,224,467 | 7/1993 | Oku | 128/6 |
| 5,273,025 | 12/1993 | Sakiyama et al. | 128/6 |

FOREIGN PATENT DOCUMENTS

| 59-88140 | 5/1984 | Japan . |
| 2-277440 | 11/1990 | Japan . |
| 3-5174 | 1/1991 | Japan . |
| 3-212262 | 9/1991 | Japan . |

Primary Examiner—Ruth S. Smith
Attorney, Agent, or Firm—Frishauf, Holtz, Goodman & Woodward

[57] ABSTRACT

There is provided an apparatus for receiving nuclear magnetic resonance signals by applying high frequency energy to a living body placed in a static magnetic field. The distal end portion of the insertion section of the endoscope has a rigid distal end portion and a bendable portion. A housing portion for housing a high frequency coil is provided between the rigid distance portion and the bendable portion. This structure makes it possible to assemble the high frequency coil into the endoscope in a compact manner and can reduce a patient's burden when the insertion section is inserted in the body cavity of the patient.

24 Claims, 17 Drawing Sheets

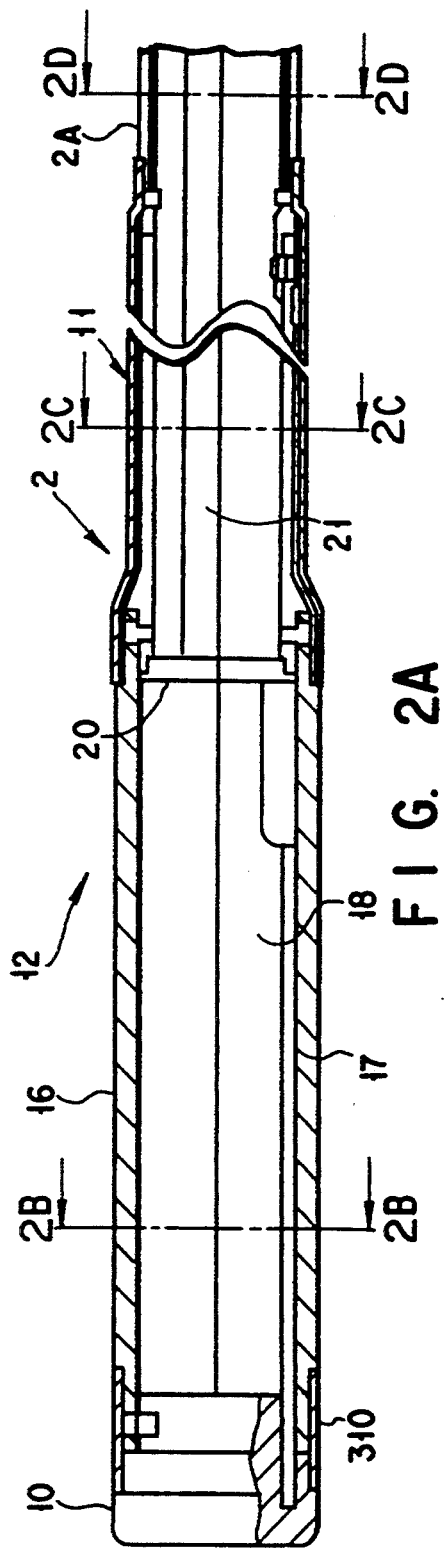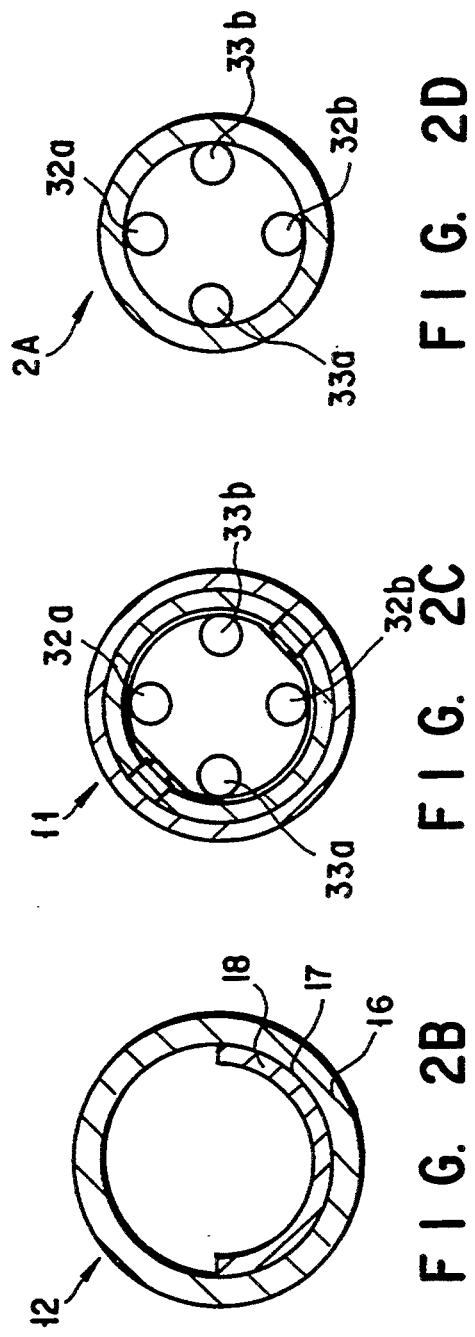

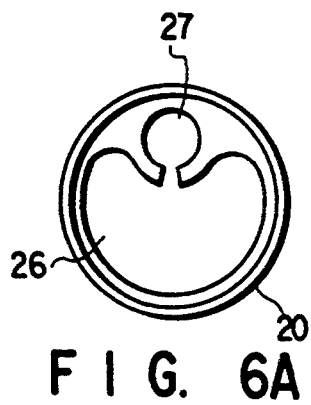
FIG. 6A
FIG. 6B
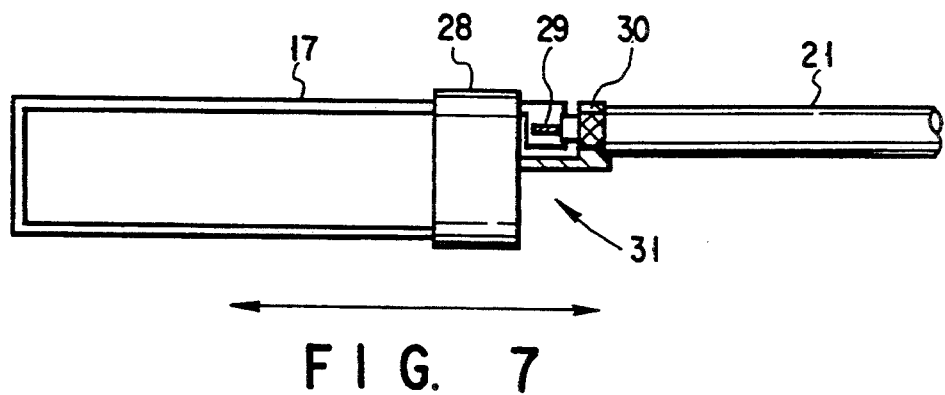
FIG. 7
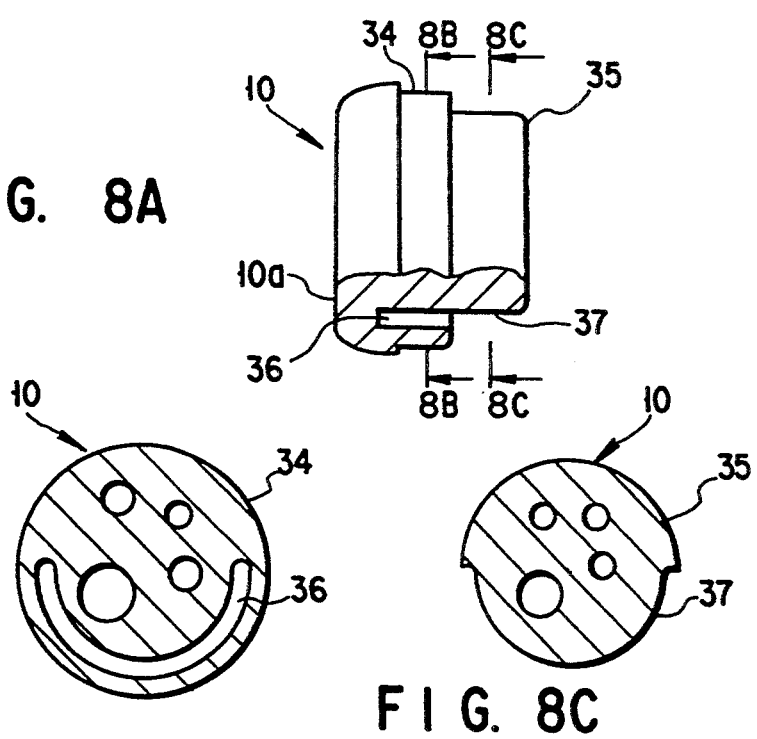
FIG. 8A
FIG. 8B
FIG. 8C

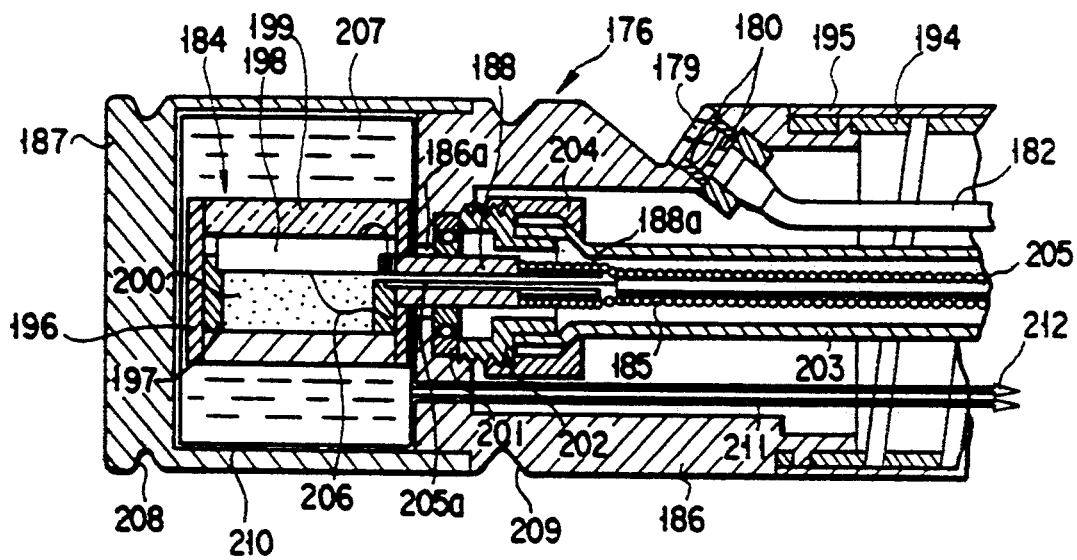
F I G. 32
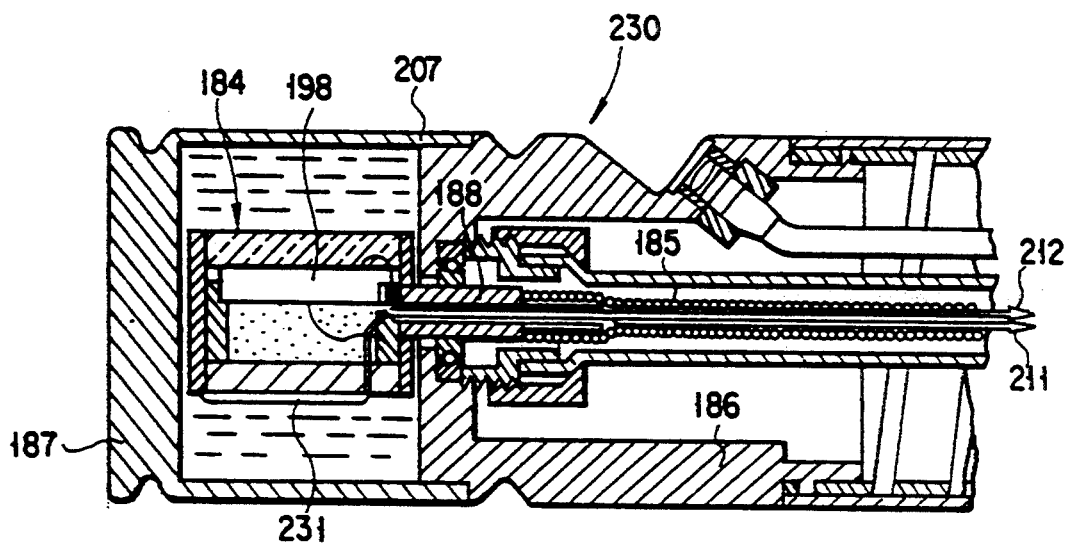
F I G. 33
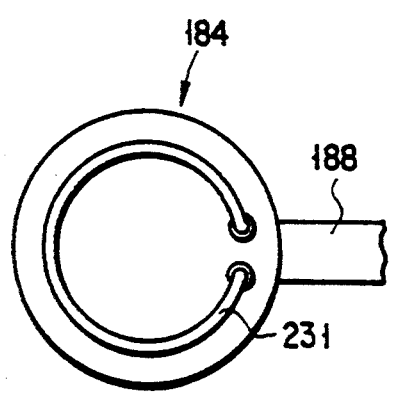
F I G. 34
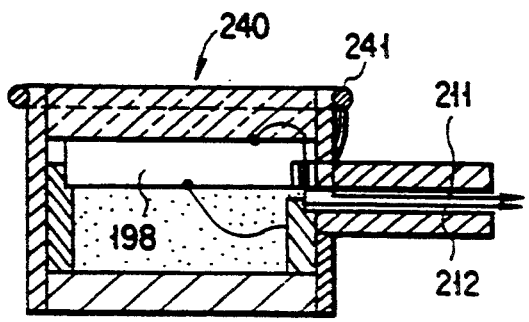
F I G. 35

MRI APPARATUS FOR RECEIVING NUCLEAR-MAGNETIC RESONANCE SIGNALS OF A LIVING BODY

BACKGROUND OF THE INVENTION

1. Field of the Invention

This invention relates to an apparatus inserted in the body cavity of a patient, for receiving nuclear-magnetic resonance signals of the living body of the patient in a static magnetic field, which signals are generated by applying high frequency energies to the living body, in use with an MRI system.

2. Description of the Related Art

There has recently been developed a non-attacking diagnosing method for a human body which utilizes a nuclear-magnetic resonance phenomenon (the nuclear-magnetic resonance being hereinafter referred to as the "MR"). With a magnetic resonance imaging device (the magnetic resonance imaging being hereinafter referred to as the "MRI"), a human body is placed in a static magnetic field, and a predetermined high frequency magnetic field is applied to the human body to excite nuclei having spins of the tissues in the body cavity of the human body. MR signals having a predetermined frequency produced until the excited nuclei return to the original positions are detected and processed by a computer to obtain cross-sectional images of the body cavity of the human body.

The cross-sectional images obtained by the MRI device are extremely effective for diagnosis such as distinction of abnormal cells such as cells suffering from cancer from normal cells. It is known that MR signals from cancer tissues and normal tissues are generated at different relaxation times. Therefore, it is possible to diagnose whether the living tissues to be examined are suffering from cancer or not by measuring and imaging the MR signals based on the relaxation time, without picking them up.

Fine and accurate images must be obtained to diagnose diseases of the digestive system such as a tubular viscus and particularly to find the depths of its affected portions. However, since the MR signal receiving coil is provided externally of a patient body with the conventional apparatus, it is difficult to obtain fine and accurate cross sectional images of deep portions of the tubular viscus of the patient. For example, with a conventional system, a surface coil for receiving MR signals is placed on the abdomen of a patient and receives MR signals to diagnose the stomach walls. However, the signal-to-noise ratio (hereinafter referred to as the "SN ratio") is too low to obtain images sufficient for required diagnosis.

In order to overcome this problem, there has been proposed an insertion apparatus such as an endoscope or a probe, which is provided, on the distal end of an insertion section inserted in the body of a patient, with an MR signal receiving high frequency coil, for detecting MR signals, as disclosed in Published Examined Japanese Patent Application No. 3-5174 and Published Unexamined Patent Application No. 2-277440. With them, a coil inserted in the patient's body receives MR signals and provides fine and accurate images having a good SN ratio. Thus, fine and accurate images can be obtained for diagnosing the depths of affected portions of tubular viscus.

when an MR signal receiving high frequency coil is provided on the distal lend portion of the insertion section, it is demanded that the opening of the high frequency coil be made as large as possible. For example, the scanning range swept by the MRI device is widened when the coil opening is rectangular and long, and the SN ratio is improved when the area of the coil opening is large. These features give advantages to MR diagnosis.

In case, however, when an observation optical system, an illumination optical system and the like are assembled into the distal end portion of the endoscope insertion section inserted in the patient's body, the outer diameter of the distal end portion of the endoscope insertion section and the rigid part of the distal end portion become large. Thus, the conventional MR endoscope in which the MR signal receiving coil is provided gives a heavy burden to the patient.

It is, therefore, demanded that technology should be developed for assembling an MR signal receiving coil, in a compact manner, into the insertion portion of an insertion instrument such as an endoscope or a probe which should be thin for relieving a burden to the patient.

SUMMARY OF THE INVENTION

The object of this invention is to provide an MRI systemized apparatus, such as an MR endoscope, for receiving nuclear-magnetic resonance signals of a living body, which portion includes an insertion member having an insertion section with a small outer diameter and a distal end section having a short rigid portion such that a high frequency coil for receiving magnetic resonance signals can be mounted in the insertion member in a compact manner thereby relieving a patient's burden when the insertion member having the coil mounted therein is inserted into his body cavity.

According to this invention, there is provided an apparatus for receiving nuclear-magnetic resonance signals produced by applying a high frequency energy to a living body disposed in a static magnetic field in use with an MRI system, which comprises:

- an elongated insertion member having a distal end portion inserted in the living body, a proximal end portion provided externally of the living body, a rigid portion provided on the distal end portion and having an axis, and a bendable portion provided closer to the proximal end portion than to the distal end portion;
- operating means extending through the insertion member and operated at the proximal end portion so as to bend the bendable portion to move the rigid portion transversely of the axis thereof; and
- receiving means provided between the rigid portion and the bendable portion, for receiving the nuclear-magnetic resonance signals, the receiving means including a casing having axially extending end portions and provided between the rigid portion and the bendable portion and a high frequency coil fixedly mounted in the casing.

The high frequency coil receives magnetic resonance signals within the body cavity. The coil is fixedly mounted in the casing provided between the rigid portion and the bendable portion. Thus, the coil can be assembled in the insertion member without enlarging the outer diameter of the insertion member of the magnetic resonance signal receiving apparatus such as an endoscope and without lengthening the rigid portion provided on the distal end portion of the insertion member.

This structure relieves the patient's burden when the insertion member is inserted in his body cavity.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a general longitudinal cross-section view of the distal end portion of the insertion section of the endoscope shown in FIG. 1;

FIG. 2B is a cross sectional view along line 2B—2B of FIG. 2A;

FIG. 2C is a cross sectional view along line 2C—2C of FIG. 2A;

FIG. 2D is a cross sectional view along line 2D—2D of FIG. 2A;

FIG. 6A is a general front view of a high frequency signal line fixing member;

FIG. 6B is a general side view of the high frequency signal line fixing member;

FIG. 7 is a plan view of a connecting portion between a high frequency coil and the high frequency signal cable;

FIG. 8A is a side view, partially cross-sectioned, of the rigid part of the distal end portion of an insertion section;

FIG. 8B is a cross sectional view along 8B—8B of FIG. 8A;

FIG. 8C is a cross sectional view along 8C—8C of FIG. 8A;

FIG. 32 is a longitudinal cross-sectional view of the distal end portion of the insertion section of the endoscope apparatus of FIG. 31;

FIG. 33 is a longitudinal cross-sectional view of the distal end portion of the insertion section of the endoscope apparatus of FIG. 31 with the arrangement of the loop antenna being modified;

FIG. 34 is a view of an ultrasonic oscillating portion as viewed from the bottom of FIG. 33; and FIG. 35 is a longitudinal cross-sectional view of a modified ultrasonic oscillating portion.

DETAILED DESCRIPTION OF THE PREFERRED EMBODIMENTS

A first embodiment of this invention will be described with reference to FIGS. 1 to 11.

Figure 1:
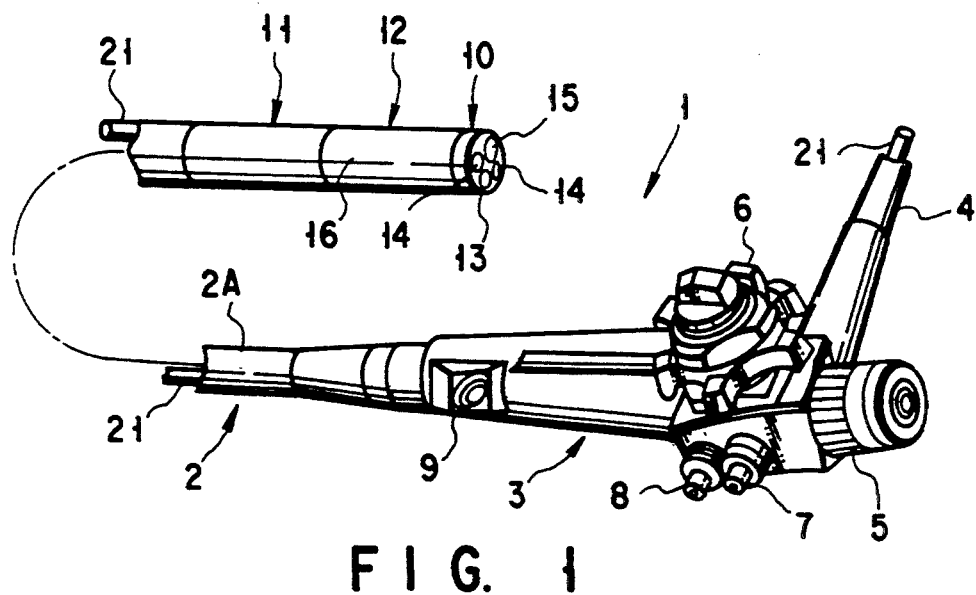
FIG. 1 is a general perspective view of an endoscope which is one embodiment of an apparatus according to this invention.

In FIG. 1 is shown an endoscope 1 in which is mounted a high frequency coil in use with an MRI device, for receiving magnetic resonance signals. Like an ordinary optical endoscope, the endoscope 1 comprises an insertion section 2 inserted in the body cavity of a patient and an operator's side operation section 3 connected to the proximal end of the insertion section 2. From the operation section 3 extends a universal cord 4 which is connected to a light source device (not shown).

The operation section 3 is provided with an ocular portion 5, an angle adjusting knob 6, a suction button 7, an air-water supplying button 8 and a forceps inlet 9 at which endoscope forceps or a treating instrument is inserted in the body cavity.

The insertion section 2 and the universal cord 4 are provided with flexible thin mounting tubes. The insertion section 2 comprises a long flexible portion 2A, a rigid distal end portion 10 provided on the extreme distal end of the insertion section, a bendable portion 11 for changing directions of the rigid distal end portion 10 and a rigid, high-frequency coil housing portion 12 provided between the rigid distal end portion 10 and the bendable portion 11. In the rigid distal end portion 10 are provided an optical system including objective lenses (objective lens system) 13 and optical guides 14, and a forceps outlet 15.

FIGS. 2A to 2D show a general internal structure of distal end part of insertion section 2, in which internal endoscope elements such as the optical system, the image guides., the light guides, the forceps channel and the like housed in the rigid distal end section 10 are not shown.

As shown in FIG. 2A, the distal end part of the insertion section 2 of the endoscope 1 has the rigid distal end portion 10 having the optical system, the high-frequency coil housing portion 12 and the bendable portion 11 arranged in this order from the distal end of the insertion section 2.

As depicted in FIG. 2B, a high frequency coil 17 for receiving MR signals (for magnetic resonance observation) is mounted in a cylindrical casing or a cylindrical body 16 made of rigid material and forming the high-frequency coil housing portion 12.

Figure 3A:
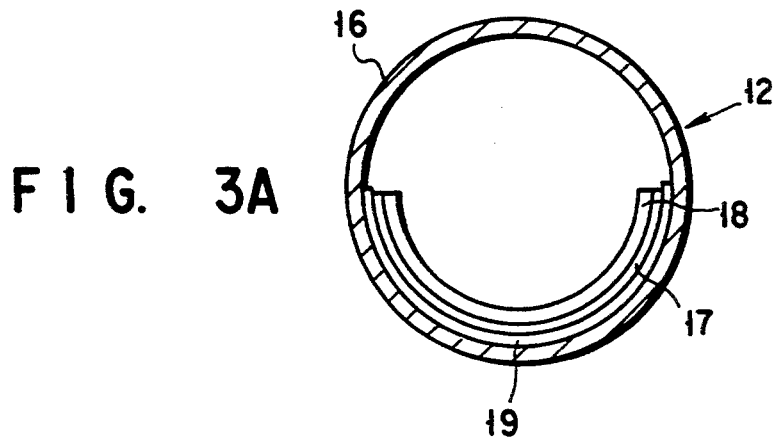
FIG. 3A is a transverse cross-sectional view of a high frequency coil receiving section.
Figure 3B:
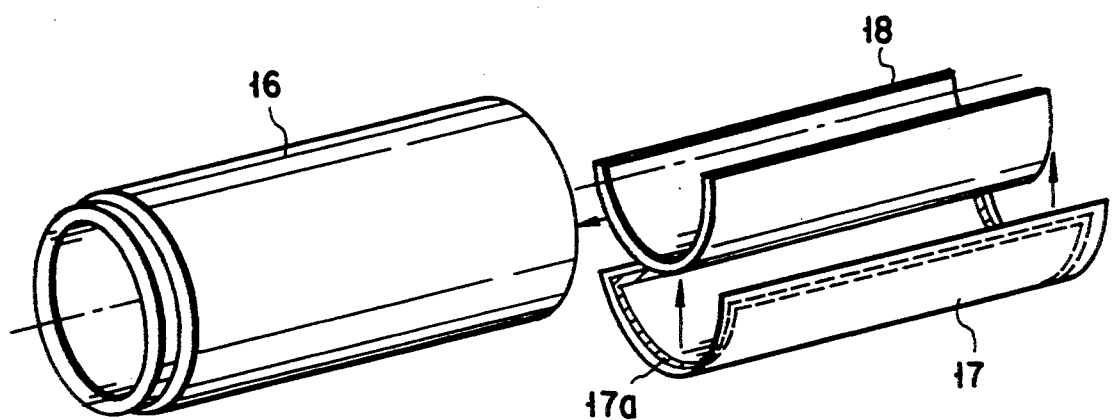
FIG. 3B is an exploded perspective view of the high frequency coil housing section.

Detailed in FIGS. 3A and 3B, the high frequency coil 17 is a sheet member. It is made by, for example, forming an MR signal receiving coil element 17a made of an electrical conductor on a soft circuit substrate such as a flexible substrate. In the cylindrical body 16 is provided an arcuated high-frequency coil fixing member 18 having a substantial arcuated form in cross-section, as well as the internal endoscope elements. The high frequency coil 17 is disposed on the outer peripheral surface of the high-frequency coil fixing member 18 and fixed thereto. The outer peripheral surface of the high frequency coil 17 is disposed on the inner peripheral surface of the cylindrical body 16 and bonded thereto by means of an adhesive layer 19. As shown in cross section in FIG. 3A, therefore, the cylindrical body 16, the adhesive layer 19, the high-frequency coil 17 and the high-frequency coil fixing member 18 are arranged radially in this order in the high-frequency coil housing portion 12.

The high frequency coil 17 is curved in conformity with the inner diameter of the cylindrical body 16 of the high-frequency coil housing portion 12 and extends along the circumference of the cylindrical body 16 over substantially a half its circumferential length. The area of the opening of the high-frequency coil 17 projected in the direction perpendicular to its axial direction is made equivalent to the area of the opening of a flat opening coil having an opening width equal to the inner diameter of the cylindrical body 16 when the flat opening coil is disposed coaxially with the central axis of the high-frequency coil housing portion 12 which central axis is directed in the insertion direction of the housing portion 16.

In the outer peripheral surface of the high-frequency fixing member 18 may be formed a coil receiving groove in which high frequency coil material made of electrically conducting material is disposed. In this case, the high frequency coil 17 is provided within the fixing member 18. The fixing member 18 which contains the high frequency coil 17 may be bonded to the inner wall surface of the cylindrical body 16.

The distal end portion of the high frequency coil 17 as well as the fixing member 18 is inserted in a groove formed in a rigid main body 10a as described later with reference to FIGS. 8A to 8C.

Figure 4:
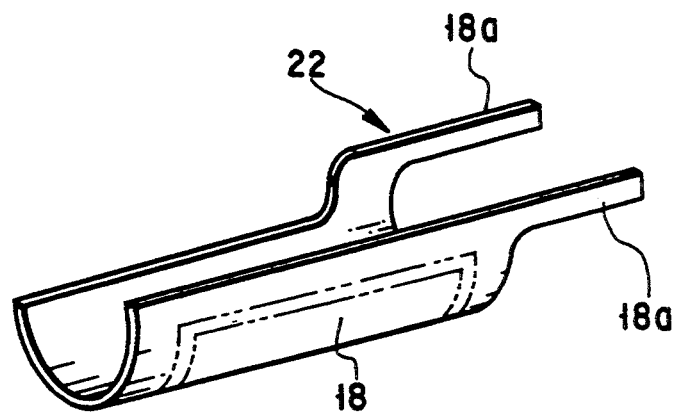
FIG. 4 is a perspective view of a modified high frequency coil fixing member of the high frequency coil housing section.

Shown in FIG. 4 is a modification of the fixing member 18 which has a pair of rearward extending supporting arms 18a and an assembling portion 22 wider than the fixing member of the high frequency coil 17.

Connected to the assembling portion 22 is a connecting portion which connects a later-described frequency signal line 21 for transmitting the received high frequency signals to an matching circuit for equalizing the impedance of the high frequency coil 17 to the impedance of the high frequency signal line 21. The rear ends of the supporting arms 18a extend to the ends of both sides of the part mounting portion. When the mounted parts such as the matching circuit and the high frequency signal line 21 are arranged not in an axial direction but in a circumferential direction by the extended rear ends of the supporting arms 18a, the mounted parts such as the matching circuit and the high frequency signal line 21 can be fixed to the assembling portion 22 at a required strength.

The length of the rigid part of the distal end portion of the insertion section 2 substantially defined originally by the length of the high-frequency coil fixing member 18 does not become so much longer when the parts such as the matching circuit and the connecting portion between the matching circuit and the high frequency signal line 21 are mounted on the high-frequency coil fixing member 18, and the length of the opening of the high frequency coil 17 can be set to a suitable value, with the rigid part of the distal end portion of the insertion section 2 of the endoscope 1 being shortened. With this structure, therefore, a burden given to a patient can be reduced when the endoscope 1 is inserted in his body cavity, and the inserting properties and operability of the insertion section 2 of the endoscope 1 can be improved.

Figure 5A:
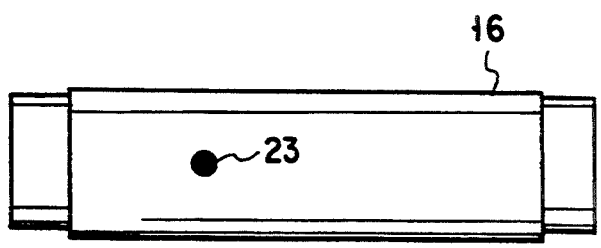
FIGS. 5A to 5C are plan views of examples of marks formed on the outer peripheral surface of the outer cylinder of the high frequency coil housing section.
Figure 5B:
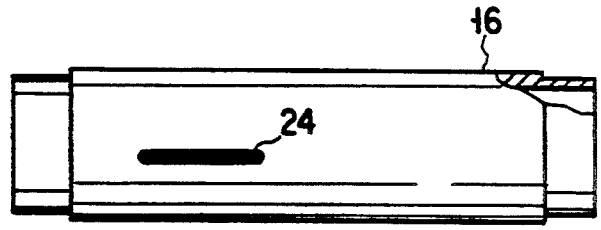
Figure 5C:
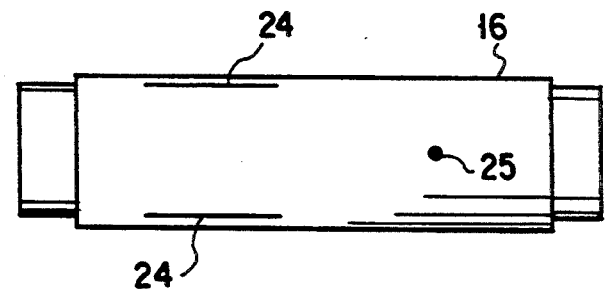

The outer peripheral surfaces of the cylindrical bodies 16 of the high-frequency coil housing portion 12 are shown in FIGS. 5A to 5C.

As shown in FIG. 5A, a center indicating mark 23 indicating the central position of the high frequency coil 17 is formed on the outer peripheral surface of the cylindrical body 16 of the high-frequency coil housing portion 12 such that the operator can visually know at what position the high frequency coil 17 is located. The center indicating mark 23 is shown right above the position at which the high-frequency coil 17 is fixed.

As shown in FIG. 5B, a width mark 24 showing the width of the high frequency coil 17 is formed on the outer peripheral surface of the cylindrical body 16 of the high-frequency coil housing portion 12. In FIG. 5C, a rear end indicating mark 25 showing the rear end position of the high frequency coil 17 is formed on the outer peripheral surface of the cylindrical body 16 of the high-frequency coil housing portion 12. The marks showing the positions of the high frequency coil 17 may be provided on the rigid distal end portion 10. Any type of marks can be used as long as they can be observed visually.

As shown in FIG. 2A, a high-frequency signal line fixing member 20 is fixed to the rear end of the high frequency coil fixing member 18 and holds an end of the high frequency signal line 21 such as a coaxial cable for transmitting signals sent and received by the high frequency coil 17. The high frequency signal line 21 extends through the bendable portion 11, a flexible tube portion 2A, the operation section 3 and the universal cord 4 and the other end of the signal line 21 is connected to the main body of an external MRI device (not shown).

FIGS. 6A and 6B show a fixing member 20 for holding the high frequency signal line 21. An inlet 26 of the internal endoscope elements and an inlet 27 of the high frequency signal line 21 are formed in the fixing member 20. After the high frequency signal line 21 has been connected to the high frequency coil 17, its inserted portion is connected to the inlet 27 under pressure or bonded thereto. Thereafter the high-frequency signal line fixing member 20 is fixedly held between the high-frequency coil housing portion 12 and the bendable portion 11.

Since the high frequency signal line 21 is securely held by the fixing member 20 in this way, an extensional force applied to the high frequency signal line 21 when the bendable portion 11 is bent can be prevented from being transmitted to the connecting portion between the high frequency coil 17 and the high frequency signal line 21. Thus, when the bending is repeated, problems of the high frequency coil 17 being poorly connected to the high frequency signal line 21 and the received high frequency signals have come not being transmitted can be avoided. This improves the reliability of the connecting portion between the high frequency coil 17 and the signal line 21 and prevents malfunction of the MR device due to the bending of the endoscope 1.

In FIG. 7 is shown a connecting portion between the high frequency coil 17 and the high frequency signal line 21. Between the high frequency signal line 21 and the high frequency coil 17, a matching circuit 28 is fixed to the high frequency signal line fixing member 20. The high frequency signal line 21 of this embodiment is a coaxial cable comprising a core 29 and a shield line 30. The matching circuit 28 is provided with a coaxial cable connecting portion 31 which connects the core 29 and the shield line 30 of the high frequency signal line 21 to the matching circuit 28 separately in an electrically insulated state. The core 29 and the shield line 30 of the high frequency signal line 21 extend in the inserting direction and are connected to the coaxial cable connecting portion 31 by soldering, pressing or the like.

As shown in FIGS. 2C and 2D, angle ropes 32a, 32b, 33a and 33b for bending the bendable portion 11 are arranged in the bendable portion 11 and the flexible tubular portion 2A. The ropes 32a and 32b are U/D angle ropes for bending the bendable portion 11 upward and downward, and the ropes 33a and 33b are R/L angle ropes for bending the bendable portion 11 rightward and leftward. In general, the vertical directions are taken as the basic directions when the operation of an endoscope is explained.

The U/D angle ropes 32a and 32b are arranged at the upper position and the lower position circumferentially separated through 180°. The R/L angle ropes 33a and 33b are circumferentially separated through 90° from the U/L angle ropes 32a and 32b, respectively, and arranged at the right side and the left side of the high frequency coil 17. In this case, the plane including the axes of the U/L angle ropes 32a and 32b and the plane including the axes of the R/L angle ropes 33a and 33b coincide with each other on the insertion axis of the high frequency coil 17 at right angles. The high frequency coil 17 in the high-frequency coil housing portion 12 has an open face directed in vertical directions in which the endoscope 1 is bent such that the high frequency coil 17 for magnetic resonance observation is directed toward the vertical bending directions of the endoscope 1 so as take the most sensitive posture.

FIGS. 8A to 8C show the rigid distal end portion 10. As shown in FIG. 8A, an intermediate diameter potion 34 is formed on the rear end of the main portion 10a of the rigid distal end portion 10 and a small diameter portion 35 is formed on the rear end of the intermediate diameter portion 34 such that the outer diameter of the rigid distal end portion 10 is reduced toward the rear side. The distal end of the cylindrical body 16 of the high-frequency coil housing portion 12 is fitted on the rear small diameter portion 35, and a connecting ring 310 for connecting the portion 10a of the rigid distal end portion 10 to the cylindrical body 16 is fitted onto the intermediate diameter portion 34 (FIG. 2A).

As shown in FIG. 8B, an arcuated high-frequency coil receiving groove 36 is formed in the main portion 10a of the rigid distal end portion 10 on the distal end of the high-frequency coil housing portion 12. The groove 36 opens at the rear end of the intermediate diameter portion 34. As shown in FIG. 8C, the outer peripheral surface of the small diameter portion 35 is formed with a high-frequency coil receiving depression 37 which is continuous to the high-frequency coil receiving groove 36. The distal end portion of the high frequency coil 17 as well as the high-frequency coil fixing member 18 are inserted in the high-frequency coil receiving groove 36.

Figures 9A, 9B:
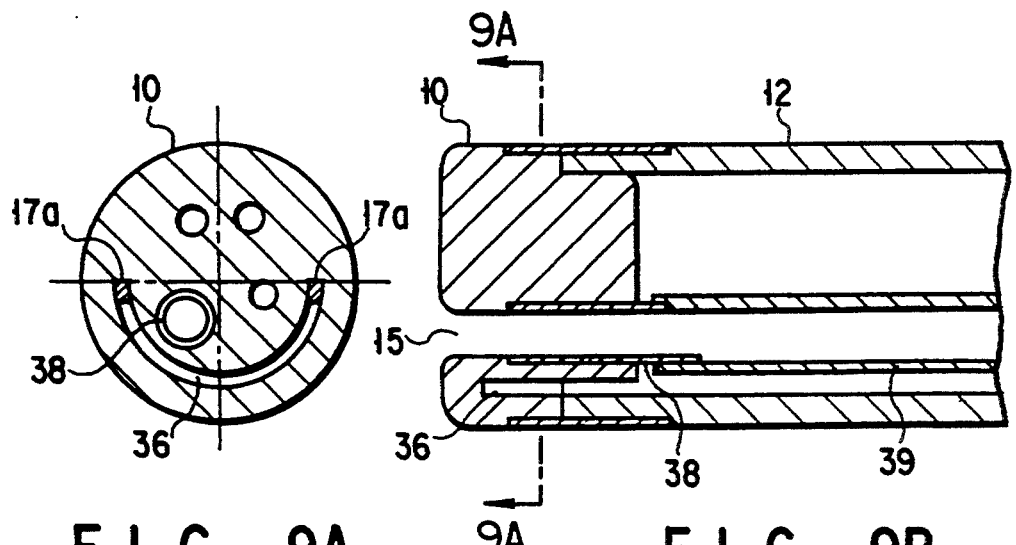
FIG. 9A is a general transverse cross-sectional view of a connecting portion between the rigid part and the high frequency coil housing section.
FIG. 9B is a general longitudinal cross-sectional view of the connecting portion between the rigid part and the high frequency coil housing section.

As shown in FIG. 9A and 9B, one end portion of a non-magnetic metal tube 38 communicating with the forceps outlet 15 is held in the main portion 10a of the rigid distal end portion 10. The distal end of a channel tube 39 through which forceps extend is connected to the other end of the metal tube 38 extending projecting from the main portion 10a toward the proximal end side. The proximal end of the channel tube 39 is connected to the forceps outlet 9 (FIG. 1). The connecting portion of the metal tube 38 to the channel tube 39 is provided on the open face of the high frequency coil 17. In this case, the metal tube 38 is placed at a separated position from the open face of the high frequency coil 17 and the electric conductor 17a forming the loop of the high frequency coil 17.

Since the metal tube 38 is disposed at a position separated from the high frequency coil 17, the signal receiving sensitive characteristic of the high frequency coil is not disturbed by the metal tube 38 which is one of the metal elements housed in the endoscope. Due to the fact that the signal receiving sensitive characteristic is not affected, a predetermined signal receiving characteristic and MR images without distortion can be obtained with the high frequency coil 17 housed in the endoscope 1. Further, the metal tube 38 which contacts the body liquid of the patient is separated from the high frequency coil 17. Thus, this structure provides a sufficient spatial distance to obtain a withstand voltage characteristic necessary for safety to electricity.

Figure 10:
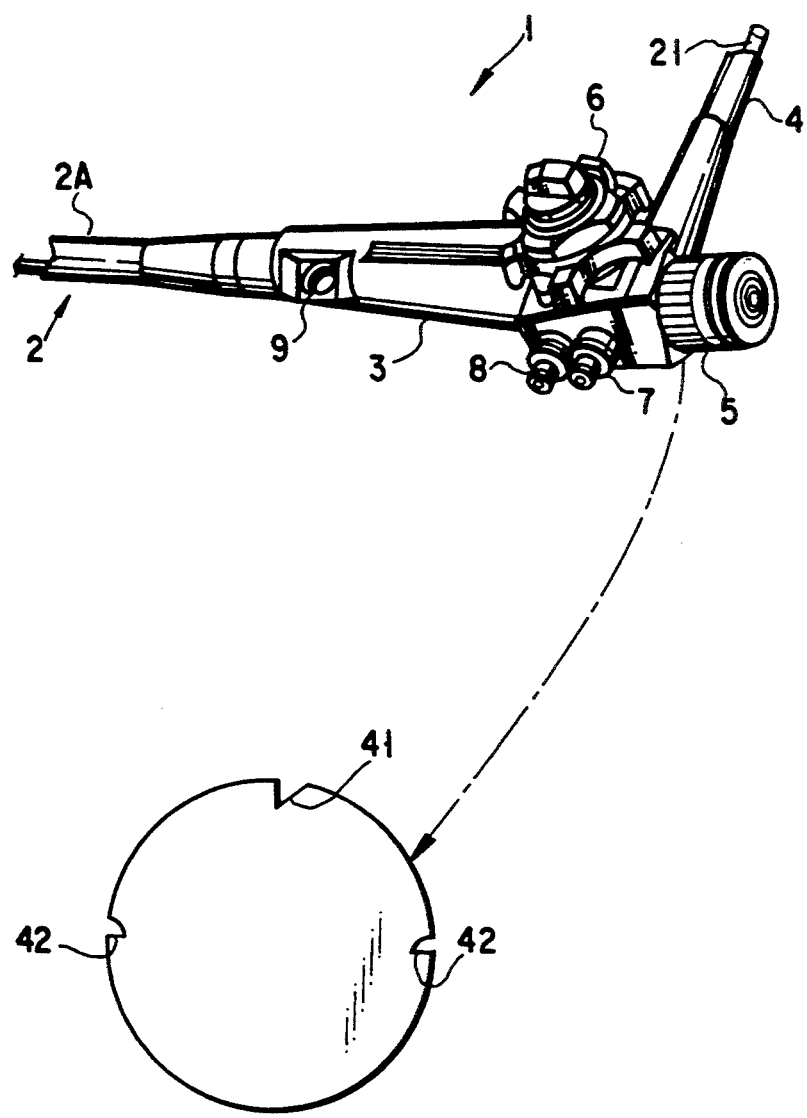
FIG. 10 is a plan view showing a visual field of the endoscope defined by a mask used in an optical system of the endoscope.

The endoscope 1 of this invention shown in FIG. 10 has an ocular portion 5 in which the ocular section side end face of an image guide fiber bundle (not shown) is placed. A visual field mask is disposed between the end face of the image guide fiber bundle and an ocular lens or an eyepiece (not shown). The visual field mask provides a visual field/of the ocular portion 5 as shown in FIG. 10. Similarly to the conventional endoscope there are provided, an upward direction mark 41 showing the upward bending direction of the endoscope 1, and coil marks 42 showing the direction and the position of the high frequency coil 17. In FIG. 10B, for example, the high frequency coil 17 is disposed in the lower half of the visual field, i.e., between the right and left coil marks 42.

Figures 11A, 11B:
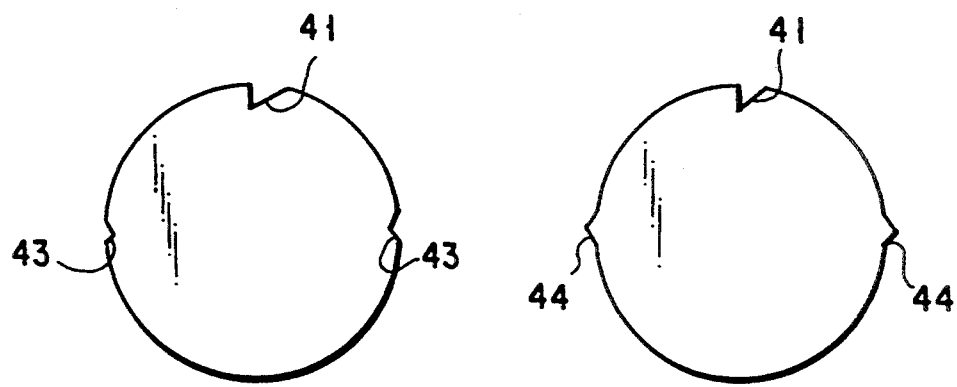
FIGS. 11A to 11D are plan views of modified marks provided for the visual fields of the endoscopes.
Figures 11C, 11D:
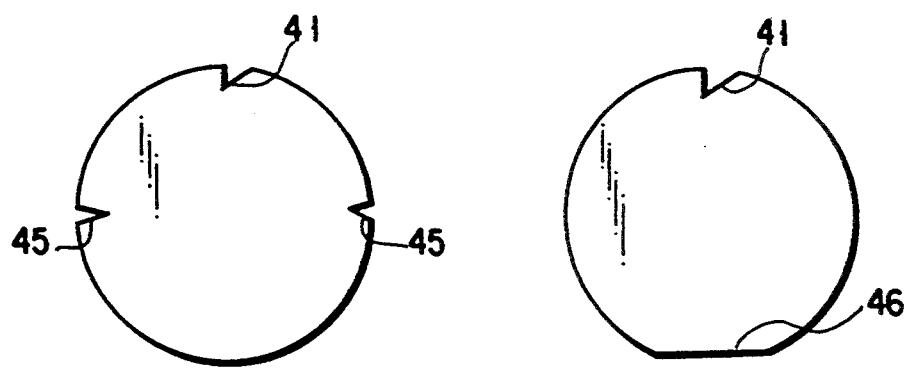

In FIGS. 11A to 11D are shown modifications of the marks in the visual field of the endoscope. FIG. 11A shows coil direction marks 43, each of which has an open angle larger than the open angle of the upward direction mark 41 or comprises a flat plane. In the modification as shown in FIG. 11B, coil direction marks 44 are formed by projections projecting toward the outside of the endoscope visual field such that the marks 44 do not disturb the visual field. Further, as shown in FIG. 11C, the open angle of the coil direction marks 45 are made sharp in order that the marks 45 disturb the visual field of the endoscope 1 as little as possible and the marks indicate the direction of the high frequency coil 17 and well. Still further, as shown in FIG. 11D, a flat portion as a mark 46 for showing only the direction of the high frequency coil 17 may be formed on the lower portion of the endoscope visual field. The visual field may be provided with marks showing both ends of the high-frequency coil 17 and a mark for only showing the direction of the coil 17.

The operation of the endoscope of the first embodiment will be described. The high frequency coil 17 mounted in the high-frequency coil housing portion 12 connected to the rigid portion 10 of the insertion section 2 is guided to the to-be-examined portion in the body cavity of a patient by observing by means of the optical system provided in the rigid distal end portion 10 of the insertion section 2. In this state, the direction of the high frequency coil 17 can be confirmed by the marks 23 to 25 formed on the outer peripheral surface of the cylindrical bodies of the high-frequency coil housing portion 12, as shown in FIGS. 5A to 5C.

At the portion of the body cavity to be examined, the bendable portion 11 is bent by the operation of the angle adjusting knob 6 to direct the high frequency coil 17 in a direction suited for MR diagnosis. In this state, the direction and the position of the high frequency coil 17 are confirmed by the marks 41 to 46, as shown in FIG. 10 and FIGS. 11A to 11D.

Thereafter, the pictures of MR images of the interior of the patient's body cavity are taken by an MRI device (not shown) to which the high frequency coil 17 in the high-frequency coil housing portion 12 is connected. Then, the portion in question is diagnosed by means of the optical images observed through the ocular portion 5 of the endoscope 1 and the MR images.

The rigid distal end portion 10, the high-frequency coil housing portion 12 and the bendable portion 11 are arranged, in this order from the distal end toward the proximal end of the insertion section 2, in the distal end part of the insertion section 2 of the endoscope 1 according to this invention (FIGS. 1 and 2). Thus, the high frequency coil 17 for magnetic resonance observation can be assembled into the insertion section 2 in a compact manner, without making the outer diameter of the insertion section 2 and the length of the rigid part of the distal end portion of the insertion section 2 large.

The high frequency coil 17 is bonded to the inner peripheral surface of the cylindrical body 16 by the adhesive layer 19, and the high-frequency coil fixing member 18 is mounted on the inner peripheral surface of the high frequency coil 17 (FIGS. 3A and 3B). Thus, the MR high frequency coil 17 can be assembled in the insertion section 2 of the endoscope 1 in a compact manner without making the outer diameter of the insertion section of the endoscope 1.

This structure can reduce a burden which the patient receives when the endoscope 1 which houses the high frequency coil 17 for magnetic resonance observation is inserted into his body cavity. With this endoscope, therefore, a very accurate diagnosis can be performed by simultaneously checking two kinds of images, i.e., optical images and MR images in a state in which the patient's burden is reduced.

A sheet shaped, soft high frequency coil 17 comprising an MR signal receiving coil circuit formed on a soft circuit substrate such as a flexible substrate is laminated on the outer peripheral surface of the high-frequency coil fixing member 18 and fixed thereto. The high frequency coil 17 is curved in conformity with the shape of the inner peripheral surface of the cylindrical body 16 of the high-frequency coil housing portion 12, inserted in the cylindrical body 16 and fixed thereto. Thus, the high frequency coil 17 is housed in the cylindrical body 16 efficiently and the endoscope can be assembled very easily. Electrical insulation and separation of the high frequency coil 17 from the internal parts of the endoscope 1 and the protection of the high frequency coil 17 are ensured. In this connection, the effective width of the opening of the high frequency coil 17 is made maximum, and the SN ratio of the received high frequency signals is also made large.

Since the rigid distal end portion 10 including the optical system and the high-frequency coil housing portion 12 are provided at the front portion of the bendable portion 11 (FIG. 1), the bendable portion 11 can be bent without changing the relative positions of the rigid distal end portion 10 including the optical system and the high frequency coil 17. This allows for alignment of the observation direction of the endoscope with the positional direction (the measurement direction) of the high frequency coil 17. Thus, the position of the high frequency coil 17 in the patient's body cavity and the relative positions of the endoscope images and the diagnosed cross section MR images can be known extremely easily.

As the high frequency coil 17 is provided in the special high-frequency coil housing portion 12, the high frequency coil 17 is not bent when the bendable portion 5 is bent, and thus the MR signal receiving characteristic is not changed.

The plane including the axes of the U/D angle ropes 32a and 32b and the plane including the axes of the R/L angle ropes 33a and 33b intersect at right angles on the insertion axis of the high frequency coil 17, and the high frequency coil 17 is mounted in the high-frequency coil housing portion 12 such that the open face is directed in the vertical bending directions of the endoscope 1 (FIG. 2A). Therefore, the high frequency coil 17 for magnetic resonance observation can be directed in the vertical bent directions of the endoscope 1, so as to take the most sensitive position.

In setting the high frequency coil 17 at the required position in the patient's body cavity under the observation by the endoscope, the endoscope operator can direct the high frequency coil toward the most sensitive vertical directions at which the operator can practically use the endoscope very easily. Thus, the operator can handle the endoscope in accordance with his using way and his feeling, whereby the endoscope is used at excellent operability and provides quick diagnosis. Further, the operator can know the accurate direction of the endoscope in the patient's body cavity easily and directly by the marks 42, 43, 44, 45 and 46 (FIG. 10 and FIGS. 11A to 11D), and can perform the direction selection and the positioning of the high frequency coil extremely effectively.

The high-frequency receiving groove 36 is formed in the main portion 10a of the rigid distal end portion 10 (FIGS. 8A and 8B) and the distal end portion of the high frequency coil 17 as well as the high-frequency coil fixing member 18 are inserted in the high-frequency receiving groove 36. Thus, even when a high frequency coil 17 having a long opening is provided in order to obtain a sufficient diagnosing area for diagnosis using MR images, the rigid portion of the distal end portion of the endoscope in not made long, facilitating reduction of the burden of the patient when the endoscope is inserted in his body cavity and maintaining inserting properties and operativeness.

Figure 12:
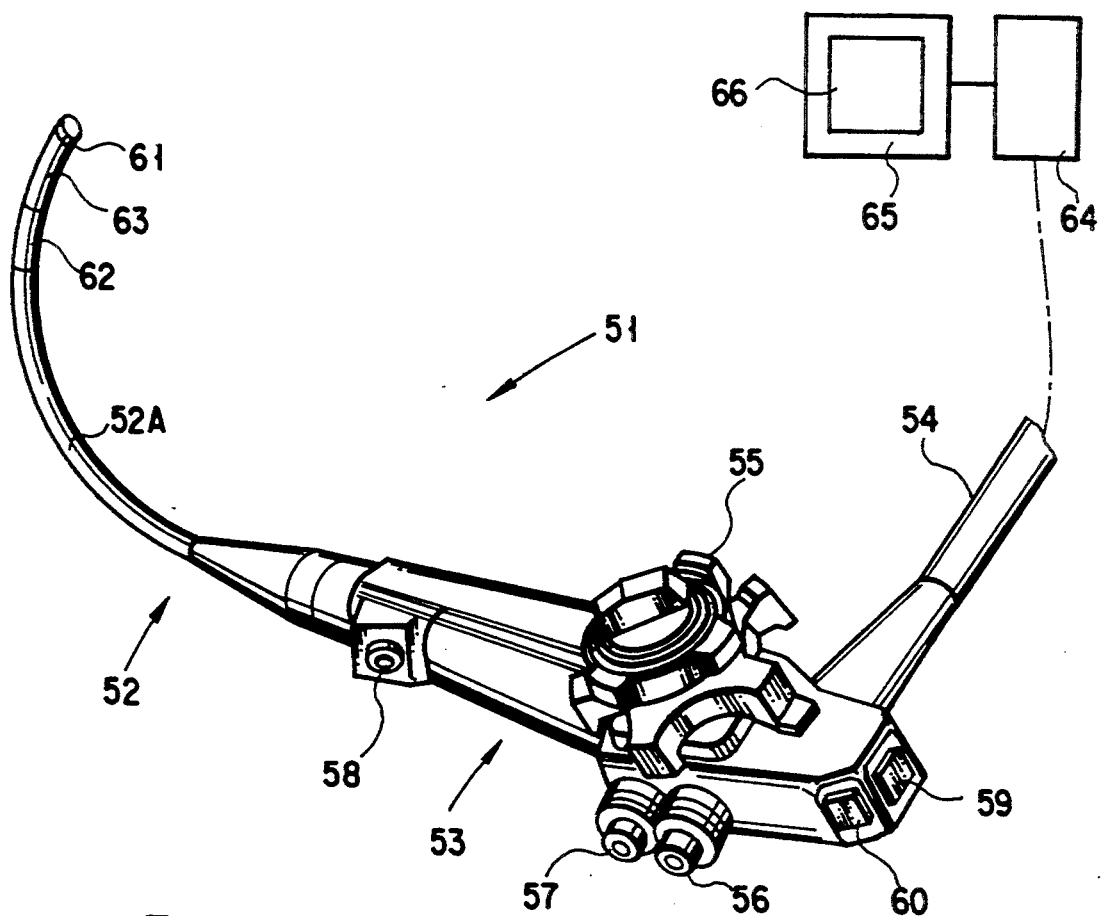
FIG. 12 is a perspective view of an electronic endoscope apparatus of another embodiment according to this invention.

FIG. 12 is a second embodiment according to this invention which is applied to an electronic endoscope. The electronic endoscope 51 includes an insertion section 52 inserted in a patient's body cavity, an operator side operation section 53 connected to the proximal end of the insertion section 52 and a universal cord 54 having one end connected to the operation section 53.

The operation section 53 is provided with an angle adjusting knob 55, a suction button 56, an air-water supplying button 57, a forceps inlet 58 at which endoscope forceps and treating instruments are inserted in the endoscope, and operating switches 59 and 60.

Similarly to the first embodiment, the insertion section 52 of the second embodiment has a long flexible tube portion 52A, a rigid distal end portion 61, a bendable portion 62 for changing the directions of the rigid distal end portion 61 and a high-frequency coil housing portion 63 provided between the rigid distal end portion 61 and the bendable portion 62.

The rigid distal end portion 61, the high-frequency coil housing portion 63 and the bendable portion 62 which the insertion section 52 comprises are arranged in this order. A rigid cylindrical body, an adhesive layer, a high-frequency coil and a high frequency coil fixing member are radially arranged in the high-frequency coil housing portion 63 in this order. The rigid distal end portion 61 is provided with an optical system and an image picking-up element such as a CCD for converting optical images into electrical signals.

Figure 13:
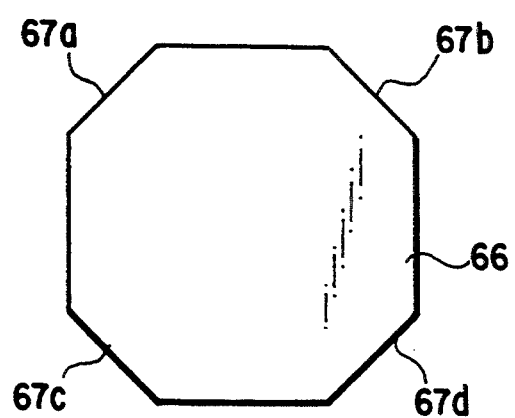
FIG. 13 is a plan view of marks provided for the visual field of a monitoring picture of the apparatus of FIG. 12.

The image signals are supplied from the image picking-up element to a control device 64 through the universal cord 54, are processed by the control device 64 and are displayed on a monitoring face 66 such as a CRT display 65. The endoscope image on the monitoring face shows a visual-field representation as shown in FIG. 13. The upper cut-out portions 67a and 67b of the representation are defined as showing the upward direction of the endoscope and they are not changed how as the operation section 53 of the endoscope 61 is rotated. The coil direction is determined by the lower cut-out portions 67c and 67d of the monitoring face.

The operation and technical advantages of the second embodiment are similar to the first embodiment. In addition, the handling, representation, processing, treating, storage and the like of the endoscope image information and the MR image information are performed extremely easily when they are correlated with each other because both information is signal information.

Each of the endoscopes of the above two embodiments has a forward viewing type optical system such that it provides an observation visual-view whose optical axis is parallel to the insertion axis of the endoscope. However, the endoscope may be of a side viewing type, having an optical system whose optical axis is perpendicular to the insertion axis of the endoscope, or of an oblique viewing type, having an optical system whose optical axis is oblique to the insertion axis of the endoscope. Needless to say, various modifications are possible within the scope of this invention.

An endoscope according to a third embodiment of this invention will be described with reference to FIGS. 14 to 19. Since the loop coil for detecting MR signals of the conventional endoscope apparatus is fixed to the insertion section of the endoscope or the front end portion of the probe, it is difficult to control the directions of the coil. For example, when the insertion section of the conventional endoscope is inserted in a patient's body cavity and the loop coil is positioned so as to obtain cross sectional images of the portions to be examined, the distal end portion containing the loop coil is moved by bending the distal end portion. However, it is sometimes difficult to arbitrarily direct the coil to the viscus to be examined depending on the inserted state of the distal end portion of the endoscope.

In this state, it is difficult to direct the coil in a direction in which the MR signals from the portions to be examined can detected suitably, i.e., in which the portion to be examined is disposed, and good MRI cross sectional images cannot be obtained.

On the contrary, with the endoscope shown in FIGS. 14 to 18, the antenna element can be directed in a suitable direction with ease in any inserted state of the distal end of the endoscope, and good MR cross sectional images can be obtained.

The endoscope equipment of this embodiment is provided with an endoscope introducing an MR antenna element into a body cavity and is intended to observe and diagnose the affected portions of a living body by means of a nuclear resonance imaging method (an MRI method). The distal end portion of the endoscope is provided with a rotary MR antenna element for receiving and sending high frequency signals and an matching circuit for matching impedance of the antenna element with the impedance of the high frequency generating means for generating high frequency signals. The MR antenna element provided in the distal end portion of the endoscope is rotated so as to be directed in a direction suited for observation and diagnosis.

Figure 14:
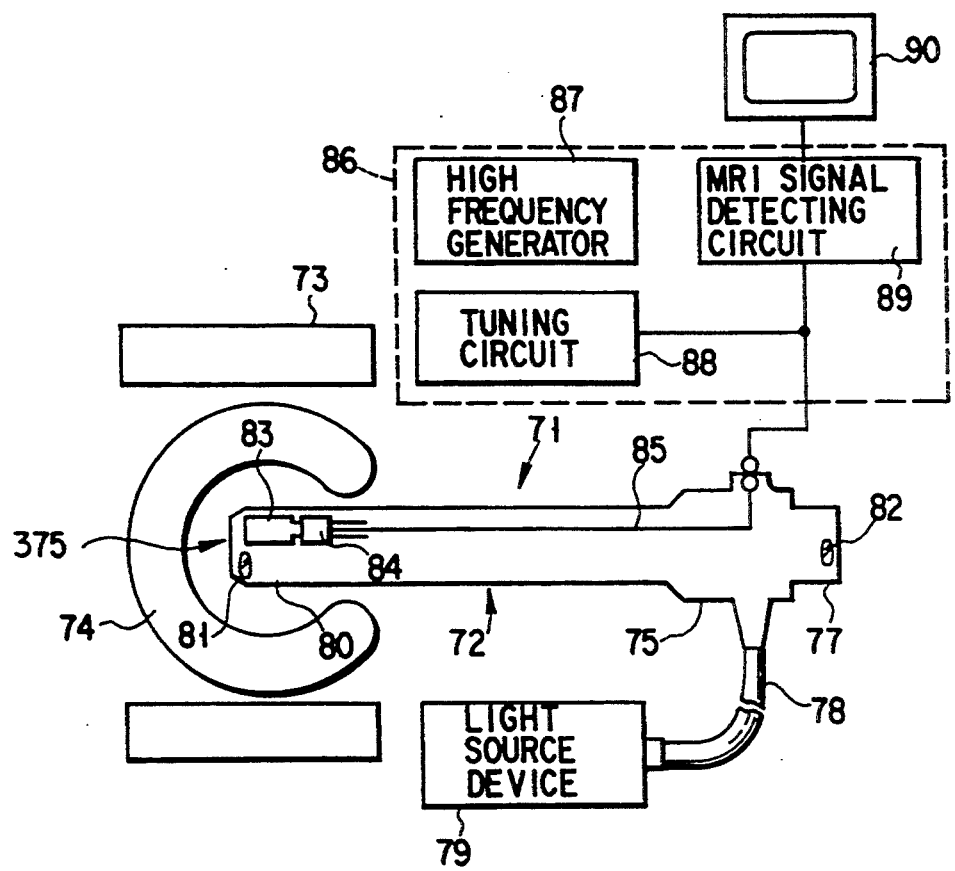
FIG. 14 is a view of an endoscope and its peripheral appliances forming a further embodiment of an endoscope apparatus according to this invention, the endoscope apparatus being designed to easily direct an antenna element in any directions irrespective of the state in which the distal end portion of the endoscope is inserted in a patient's body cavity.

As shown in FIG. 14, the endoscope 71 has an elongated flexible (for example) insertion section 72 and is adapted to be inserted in the body cavity 375 of a person to be examined or a patient placed in a static magnetic field generated by a static magnetic field generator 73 which comprises permanent magnets, normal conductive magnets or super conductive magnets.

The endoscope 71 has an operation section 75 connected to the proximal end of the insertion section 72. An ocular portion 77 is provided on the rear end of the operation section 75. A universal cord 78 extends from a lateral side of the operation section 75. The ocular portion 77 is connected to a light source device 79 by means of the universal cord 78. Illumination light transmitted by a light guide (not shown) from the light source device 79 exits from the distal end portion 80 of the insertion section 72.

An observation optical system 81 is provided in the distal end portion 80 of the insertion section 72. Optical images of the to-be-examined portion of the body cavity focused by the observation optical system 81 are transmitted by an image guide (not shown) to the operation section 75 and can be observed with the naked eye of the observer at an ocular lens 82.

In the distal end portion 80 of the insertion section 72 are provided an MR loop coil 83 as an antenna element for receiving and sending high frequency signals as will be described later, and a matching circuit 84 as means for matching impedance of the loop coil 83 with the impedance of the high frequency generating means. The loop coil 83 and the matching circuit 84 are adapted to be connected to signal lines 85 to an MRI device 86. The MRI device 86 comprises a high frequency generator 87 for generating high signals frequency, a tuning circuit 88 for tuning the frequencies of high frequency signals to the resonance frequencies of the portions of the body cavity to be examined, and an MRI signal detecting circuit 89 for detecting information (MR parameters) such as relaxation time of MR signals received by the loop antenna 83 from the portions of the body cavity to be examined and generating MRI cross sectional images such that the MRI cross sectional images are displayed on a monitor 90.

Figure 15:
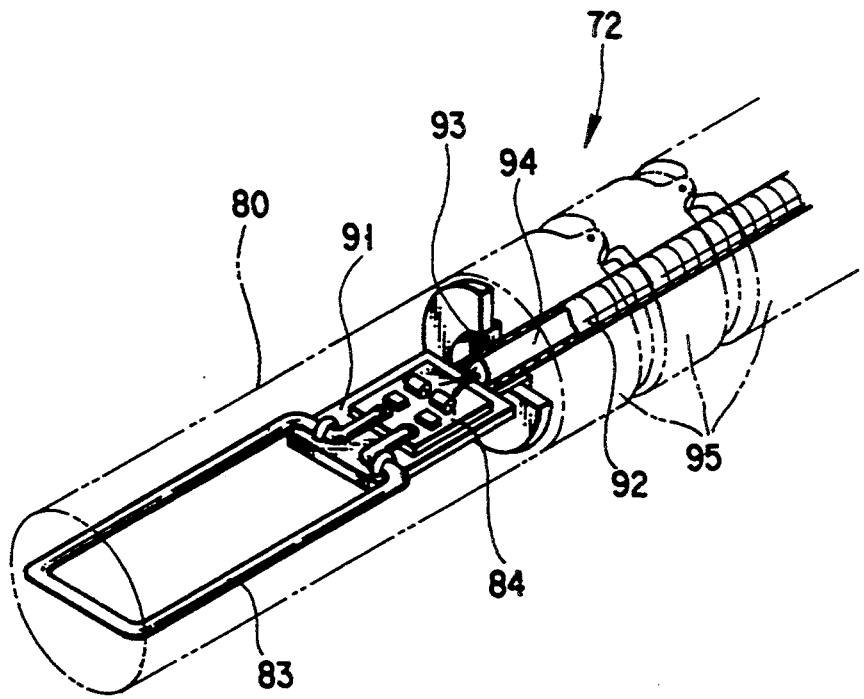
FIG. 15 is a general perspective view of the distal end portion of the insertion section of the endoscope.

The structure of the distal end portion 80 of the insertion section 72 of the endoscope 71 will be described with reference to FIG. 15. In the distal end portion 80 of the insertion section 72 is provided a substrate 91 on which the loop coil 83 and the matching circuit 84 are provided. The substrate 91 is fixed to a rotary shaft 92 which is inserted in the insertion section 72. The rotary shaft 92 comprises a bendable, flexible shaft, for example. The rotary shaft 92 is supported by a bearing 93. The substrate 91 is rotated by coil driving means provided on the proximal end portion of the rotary shaft 92 around an axis parallel to the lengthwise direction of the insertion section 72.

The rectangular loop coil 83 connected to the matching circuit 84 provided on the substrate 91 projects forward from the substrate 91 and is fixed thereto. As the rotary shaft 92 rotates, the loop coil 83 and the matching circuit 84 also rotate. A coaxial cable 94 which is the signal line 85 for transmitting high frequency signals extends through the rotary shaft 92 and is connected to the matching circuit 84. A plurality of bending pieces 95 are connected to the proximal end of the distal end portion 80 and perform a bending operation due to the pull and push of bending wires (not shown).

Figure 16A:
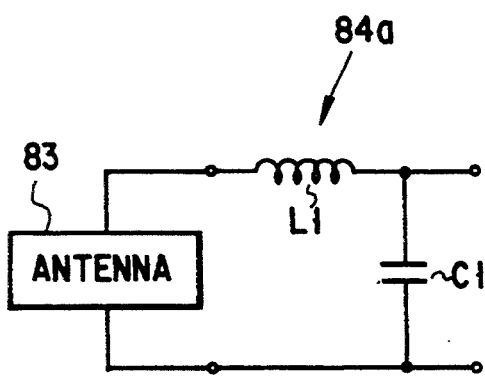
FIGS. 16A and 16B are circuit diagrams showing matching circuits of the endoscope shown in FIG. 14.
Figure 16B:
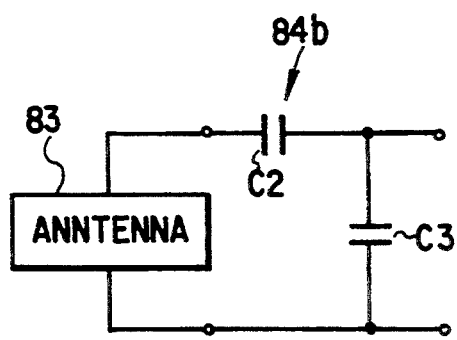

FIGS. 16A and 16B show two examples of the matching circuit 84. As shown in FIG. 16A, the first example of the matching circuit 84a comprises a coil L1 in series with the loop coil 83 and a condenser C1 in parallel to the antenna 83. As shown in FIG. 16B, the second example of the matching circuit 84b comprises a condenser C2 in series with the coil 83 and a condenser C2 in parallel to the coil 83. The impedances of the loop coil 83 and the MRI device are matched by the matching circuit 84 as shown in FIGS. 16A and 16B. Since the matching circuit 84 is directly connected to the loop coil 83, the impedance matching can be obtained just after the loop coil 83. Thus, very weak signals received, by the loop coil 83, from the portions of the body cavity to be examined can be detected well without influence such as noises.

Figure 17:
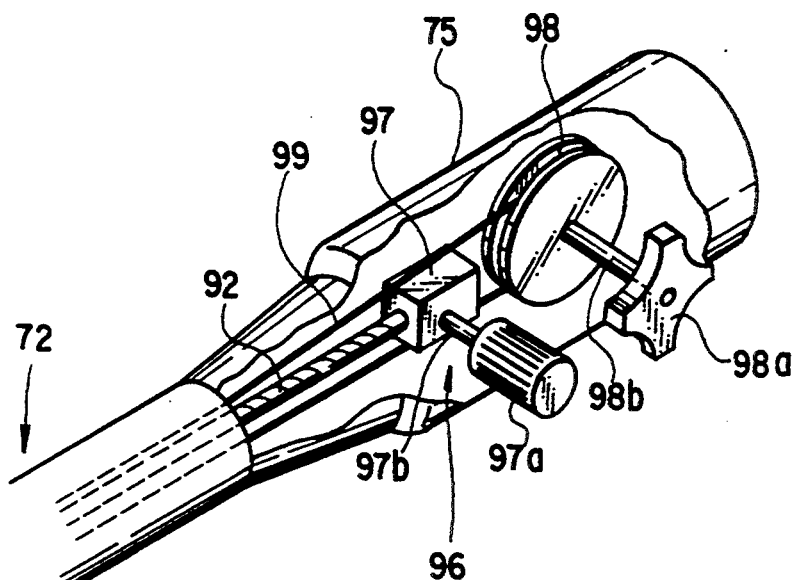
FIG. 17 is a perspective view of an operator's side end portion of the endoscope of FIG. 14.

As shown in FIG. 17, a coil driving mechanism 96 constituting coil driving means is provided in the operating section 75 provided on the proximal end of the insertion section 72. The coil driving mechanism 96 comprises a gear mechanism 97 connected to the proximal end of the rotary shaft 92 and a rotation knob 97a connected to gears in the gear mechanism 97 by a driving shaft 97b extending from the rotation knob 97a to the gear mechanism 97. As the rotation knob 97a is rotated, the rotary shaft 92 and the loop coil 83 are rotated. In the operation section 75 is provided a pulley 98 about which is wound a bending wire 99 extending through the insertion section 72 having ends connected to the bending piece 95 which is the closest to the pulley 98. A bending knob 98a is connected to the rotary shaft 98b of the pulley 98. As the bending knob 98a is rotated, the bending wire 99 is pushed and pulled so as to curve the shape of the total bending pieces 95, whereby the insertion section 72 is bent.

The operation of this endoscope apparatus will be described.

In making MR diagnosis, the person to be examined or the patient 74 is placed in a static magnetic field generated by the static magnetic field generator 73, and the MR endoscope 71 is inserted in his body cavity 375 to its portion to be examined by observing optical image through the observation optical system 81 and the ocular portion 77. High frequency signals are sent from the loop coil 83 to the portion to be examined in the patient's body cavity and return to the loop coil 83. The NMR parameters due to the signals received as MR signals by the coil 83 from the portion of the body cavity to be examined are detected to form an MRI cross sectional image.

In this case, the loop coil 83 is turned by the operation of the rotation knob 97a of the operation section 75 and is directed toward the viscus to be examined so as to obtain the highest sensitivity of the loop coil 83. It will be explained how to diagnose a pancreas by using an endoscope inserted into a patient's stomach according to the MRI method.

Figure 18:
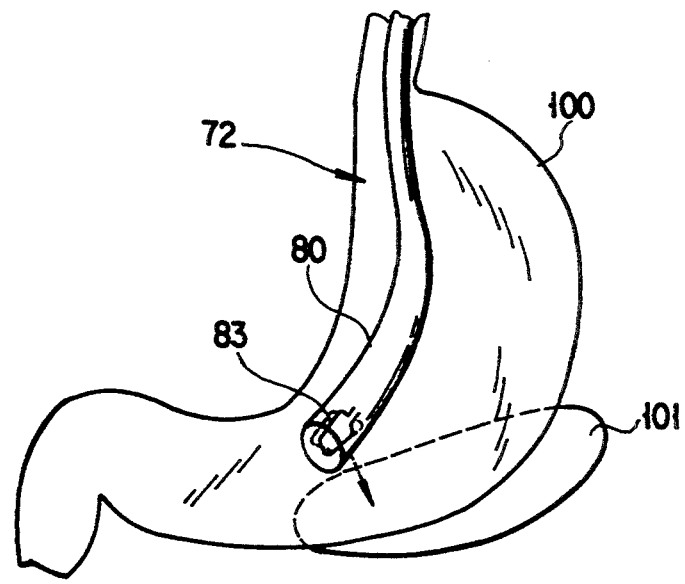
FIG. 18 is a view illustrating the state in which the endoscope is inserted in a patient's body cavity.

As shown in FIG. 18, when the insertion section 72 of the endoscope 71 is inserted in the stomach 100, the loop coil 83 generally takes a position as indicated by the solid line, at which the open face of the coil 83 is not directed toward the pancreas 101. Then, the coil 83 is turned to take a position shown by the broken line so as to make the open face of the coil 83 directed toward the pancreas 101 as shown by a broken arrow. This provides the highest sensitivity of the loop coil 83 to the pancreas 101, and good and accurate MR signals of the pancreas 101 are detected.

In this way, MRI cross sectional images are formed and diagnosis is performed after the loop coil has been directed toward the portion of the body cavity to be examined by rotating the loop coil 83. High frequency signals generated by the high frequency generator 87 are supplied via the tuning circuit 88 to the to-be-examined portion of the body cavity in a static magnetic field. The MR signals from the portion to be examined are received by the loop coil 83, and the MR parameters are detected by the MRI signal detecting circuit 89 within the MRI device 86 to form MRI cross sectional images. The output signals from the MRI signal detecting circuit 89 are input to the monitor 90 and the MRI cross sectional images of the portion to be examined are indicated by the monitor 90.

Since, therefore, the loop coil can be easily directed toward the portion of the body cavity to be examined when the distal end portion 80 of the insertion section of the endoscope 71 is directed in any direction at first, MR signals from the portion of the body cavity to be examined are detected clearly and accurately, and good and accurate MRI cross sectional images can be obtained. The matching circuit 84 is provided close to the loop coil 83. Thus, the impedance matching can be made just after the loop coil 83 such that a very weak signal from the portion of the body cavity to be examined can be detected well without receiving adverse influence such as noises.

Figure 19:
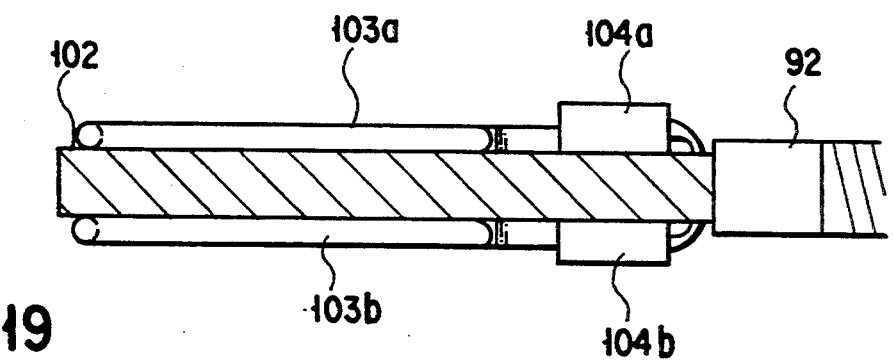
FIG. 19 is a side view of a loop antenna connected to the matching circuit and provided on the distal end portion of the insertion section of the endoscope of FIG. 14.

In FIG. 19 is shown a modification of the loop coil and the matching circuit provided in the distal end portion of the insertion section, in which two loop coils are arranged in parallel to each other. A substrate 102 on which the loop coils and the matching circuit are mounted is connected to an end of the rotary shaft 92 extending through the insertion section 72. On the respective surfaces of the substrate 102 are mounted two loop coils 103a and 103b which are connected in series and arranged in parallel and opposed to each other. Similarly, two matching circuits 104a and 104b are provided on the respective surfaces of the substrate 102 and connected to the respective loop coils 103a and 103b. The matching circuits 104a and 104b are connected to the MRI device by signal lines (not shown) extending through the rotary shaft 92.

By arranging the two loop coils 103a and 103b in parallel to each other, they are directed in the same direction, thereby improving the directivity characteristic of the loop coils. The sensitivity of the antennas when their open faces are directed toward the portion of the body cavity to be examined is improved. Thus, highly sensitive MR signals can be detected by directing the loop coils toward the object to be examined and MRI cross sectional images having a high resolution can be obtained. Further, a required directivity characteristic can be obtained by adjusting the distance between the loop coils.

The endoscope apparatuses shown in FIGS. 20 to 30 will be described, each of which is constructed so as to check whether the direction of the coil with respect to the direction of the MRI static magnetic field is suitable to obtain MRI images. The same parts and elements as those shown in the previous figures will be designated by the same reference numerals and their description will be omitted.

With the conventional endoscope containing the coil for receiving high frequency signals in the distal end portion of the insertion section, it cannot be known whether the coil is directed in such a specific direction with respect to the direction of the static magnetic field that required MRI images are obtained as long as the endoscope images are observed. Further, when the face of the coil is perpendicular to the bed inserting axis of a gantry on which a static magnetic generator is provided, MRI images can hardly be obtained. It can be known whether MRI images are obtained only after nuclear magnetic resonance scanning is performed, which wastes time. Therefore, it has been demanded that this wasted time be eliminated.

The endoscopes shown in FIGS. 20 to 30 overcome this problem. Each of these endoscopes comprises an endoscope main body having an insertion section inserted in a living body, a coil provided integral with or separately from the endoscope main body for obtaining images due to a nuclear magnetic resonance imaging method, angle detecting means for detecting an angle between the face of the loop of the coil, etc. and the static magnetic field and angle displaying means for indicating, in the vicinity of an endoscope observation image, the angle detected by the angle detecting means.

As it can be known, in the vicinity of the endoscope observation image by means of the angle detecting means, whether the MRI image can be obtained easily, trial operation for checking whether the MRI image is obtained is not required.

Figure 20:
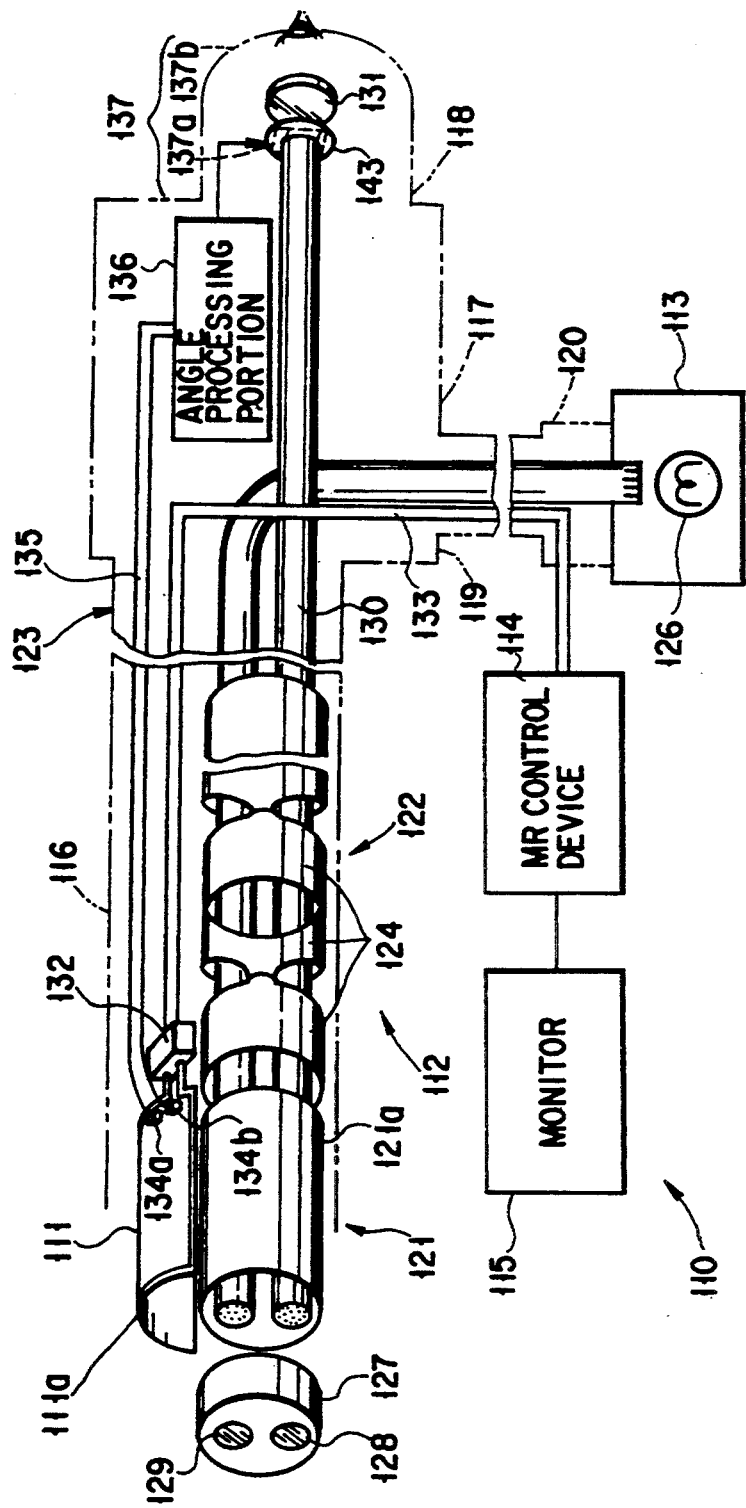
FIG. 20 shows an arrangement of the overall endoscope apparatus which is a further embodiment of this invention and can check whether the direction of an antenna makes with the direction of an MRI static magnetic field an angle at which an accurate MRI image can be obtained.

As shown in FIG. 20, an embodiment of the MR endoscope apparatus 110 comprises an endoscope 112 having a printed substrate 111 provided with a coil 111a for obtaining MRI images (hereinafter referred to as only the "coil"), a light source device 113 for supplying illuminating light to the endoscope 112, an MRI control device 114 (described also as the "MR control device" or simply the "control device"), and a monitor 115 displaying the MRI images.

The endoscope 112 has an elongated and flexible (for example) insertion section 116, to the rear end of which an operation section 117 having a large width is connected. An ocular portion 118 is formed on the rear end of the operation section 117. A light guide cable 119 extends from a lateral side of the operation section 117 and a connector 120 provided on the free end of the light guide cable 119 is connected to the light source device 113.

The insertion section 116 comprises a rigid distal end portion 121, a bendable portion 122 provided adjacent to the rear end of the distal end portion 121 and a long flexible tube portion 123 extending from the rear end of the bendable portion 122 to the operation section 117. The bendable portion 122 comprises bending pieces 124 which are bent as a unit upward or downward, or rightward or leftward by rotating a bending knob (not shown). More specifically, the bending pieces 124 are pivotally connected to one after another by means of pivotal elements such as hinge pins such that the bendable portion 122 can be bent both horizontally and vertically. By the rotation of the bending knob, one of a pair of wires (not shown) is pulled or loosened and the other wire is loosened or pulled such that the bendable portion 122 is bent toward the pulled side.

A light guide fiber bundle 125 extends through the light guide cable 119 extending from the operation section through the insertion section 116. The connector 120 is connected to the light source device 113, and illumination light generated by a lamp 126 within the light source device 113 is supplied through the light guide fiber bundle 125 to an exit face fixed to the main body 121a of the distal end portion 121 made of rigid material and is exited from an illumination lens 128 fixed to a lens fixing member 127. The image of the object or portion of a patient's body cavity illuminated with the illumination light is focused by an objective lens system 129 fixed to the lens fixing member 127 on one end face of an image guide fiber bundle 130 which end face is on the focal surface of the objective lens system 129. The focused image is transmitted to the other end face (an exit face) of the ocular portion 118 by the image guide fiber bundle 130 and magnified. Thus, the enlarged images can be observed by the observer's naked eye at the ocular portion 131.

The main body 121a of the distal end portion 121 is tubular or cylindrical. The substantially semicylindrical printed substrate 111 is mounted in the upper portion of the main body 121a of the distal end portion 121, for example. The printed substrate 111 is patterned such that a generally rectangular loop coil 111a is formed on it. The ends of the loop of the coil 111a are connected to the input terminals of the matching circuit 132. The face (hereinafter also referred to as the "coil face") including the rectangular loop of the coil 111a is made substantially parallel to the face including the horizontally arranged pivotal elements of the bending pieces 124.

When the vertical bending knob is rotated in the condition shown in FIG. 20, the bendable portion 122 is bent upward or downward at the pivotal elements, and the antenna face inclines upward or downward with respect to the horizontal plane.

The output terminal of the matching circuit 132 is connected to the control device 114 by a coaxial cable 133. The matching circuit 132 is connected to the antenna 111a and a signal sending and receiving circuit (not shown) in the control device 114 and performs impedance matching and impedance transformation.

The signal sending and receiving circuit sends RF signals from the signal sending circuit to the object or the portion of the patient's body cavity to be examined, receives magnetic resonance signals from the object, and then outputs them to the signal receiving circuit. The receiving circuit processes the received signals to produce MRI images, and the images are displayed on the monitor 115.

On the printed substrate 111 are provided first and second magnetic detecting means 134a and 134b, whose outputs are supplied to an angle processing portion 136 in the operation section 117 through signal lines 135, for example. The angle processing portion 136 is provided in the ocular portion 118, for example, and is connected by a signal line to an angle indicating portion 137 which indicates angles detected by the first and second magnetic detecting means 134a and 134b, respectively.

Figures 21A, 21B:
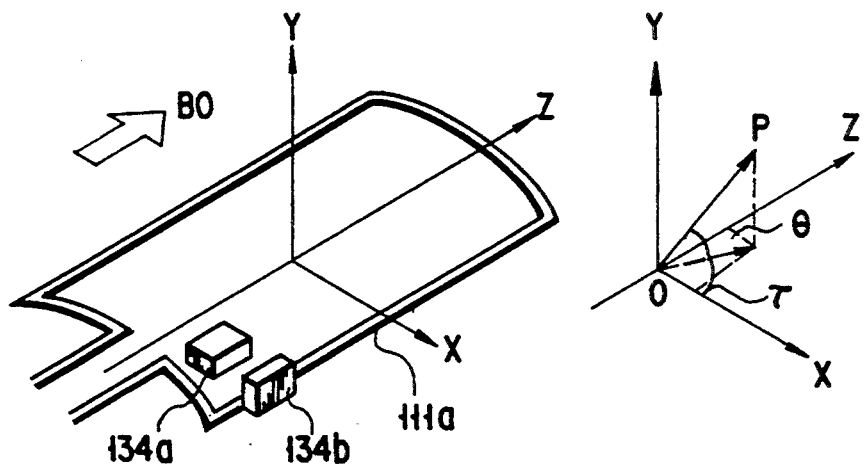
FIG. 21A is a view showing angle detecting means for detecting angle of the direction of the antenna making with the direction of the static magnetic field.
FIG. 21B is a view showing the detected angle by the angle detecting means of FIG. 21A.

As shown in FIG. 21A, the first and second magnetic detecting means 134a and 134b detect the angle between the direction of the static magnetic field BO and the coil face of the coil 111a. As shown in FIG. 21B, the direction of the static magnetic field BO in MR1 gantry is taken as the Z axis of three-dimensional orthogonal coordinates, the first magnetic detecting means 134a detects a vertically inclined angle $\theta$ with respect to the Z axis, i.e., an angle $\theta$ in the YZ plane and the second magnetic detecting means 134b detects a horizontally deviated angle $\phi$ from the X-axis, i.e., an angle $\phi$ in the XZ plane.

The first and second magnetic detecting means 134a and 134b are arranged in the following manner. When, for instance, the bendable portion 119 is bent from the state in which the antenna face of the NMR antenna 111a is set in parallel to the direction of the static magnetic field BO as shown in FIG. 21A to the state in which the bendable portion 119 is directed to a direction OP making a vertical angle of $\theta$ and a horizontal angle of $\phi$ with the Z-axis, magnetic fluxes proportional to the bent angles $\theta$ and $\phi$ pass the first and second magnetic detecting means 134a and 134b, respectively, and electromotive forces Va and Va proportional to the angles $\theta$ and $\phi$ are generated in the first and second magnetic detecting means 134a and 134b.

Figures 22A, 22B:
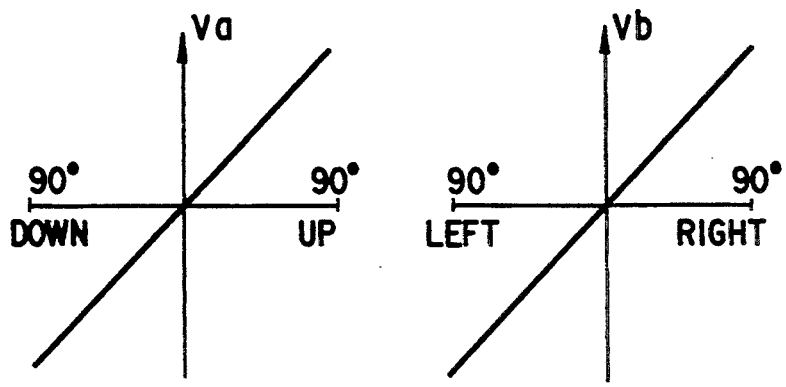
FIGS. 22A and 22B are views showing the relations between the angle detected by the two angle detecting means and detected voltages.

FIG. 22A shows the relation between the vertical angles and the electromotive forces Va and FIG. 22B shows the relation between the horizontal angles and the electromotive forces Vb. Both electromotive forces are generated in proportion to the inclined angles. From the polarities of the generated electromotive forces, it is detected that the bendable portion is bent upward or downward an/or to the right side or left side.

The electromotive forces Va and Vb are processed by the angle processing portion 136 and indicated on the angle indicating portion 137.

Figure 23:
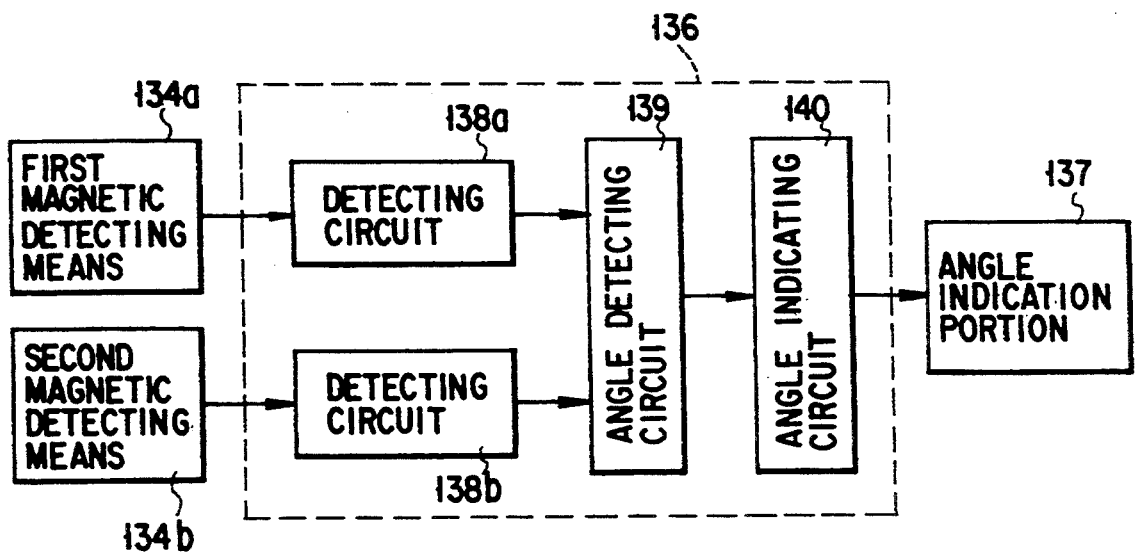
FIG. 23 is a block diagram of an angle processing portion.

FIG. 23 shows the angle processing portion 136.

The outputs of the first and second magnetic detecting means 134a and 134b are supplied to respective detecting circuits 138a and 138b constituting the angle processing portion 136 and detected as the electromotive forces Va and Vb. These electromotive forces are input to an angle detecting circuit 139 and detected as an angle. The angle is supplied to an angle indicating circuit 140 and transformed into letter information showing the angle. The information is input to the angle indicating portion 137, and a vertical angle 141b and a horizontal angle 141c are displayed together with an endoscope image 141a on a finder view field 141.

Figure 24:
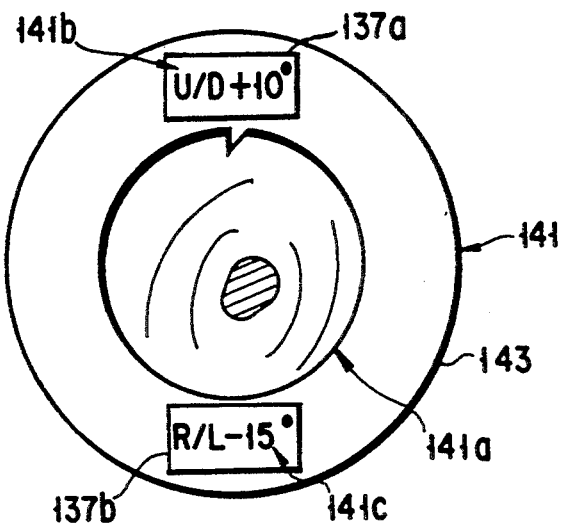
FIG. 24 is a view illustrating how to indicate the angle detected in a finder.

In this embodiment, at the end face of the image guide 130 at the side of the ocular portion 118 is provided a ring-shaped view field mask 143 for masking the other portion of the end face than the image of the end face. On the upper and lower portions of the view field mask 143 are formed a vertical angle indicating part 137a and a horizontal angle indicating part 137b, both parts constituting the angle indicating portion 137. The angles are indicated as shown in FIG. 24. In the vertical angle indicating part 137a, "+" indicates the upper-side bending direction and "−" indicates the lower-side bending direction. In the horizontal angle indicating part 137b, "+" indicates the right-side bending direction and "−" indicates the left-side bending direction. At least the insertion section 116 of the endoscope 112 is made of material other than ferromagnetic material in order to reduce the effect of the static magnetic field when the insertion section 116 is placed in the static magnetic field.

Since the inclination angle of the coil 111a with respect to the direction of the static magnetic field BO is indicated together with the endoscope image 141a on the finder view field, it is known without performing any trial operation whether an MRI image can be obtained. Further, the bendable portion is bent so that the bending angles which are indicated on the angle indicating portion become zero or substantially zero in order to obtain an accurate MRI image. In this way, the bendable portion can quickly be set to the position at which the MRI image is obtained without performing any trial operation.

The face including the coil 111a is set in parallel to the horizontal direction of the bendable portion 122. Thus, the bendable portion 122 can be easily and quickly set by the bending operation to a state in which the MRI image is obtained.

Figure 25:
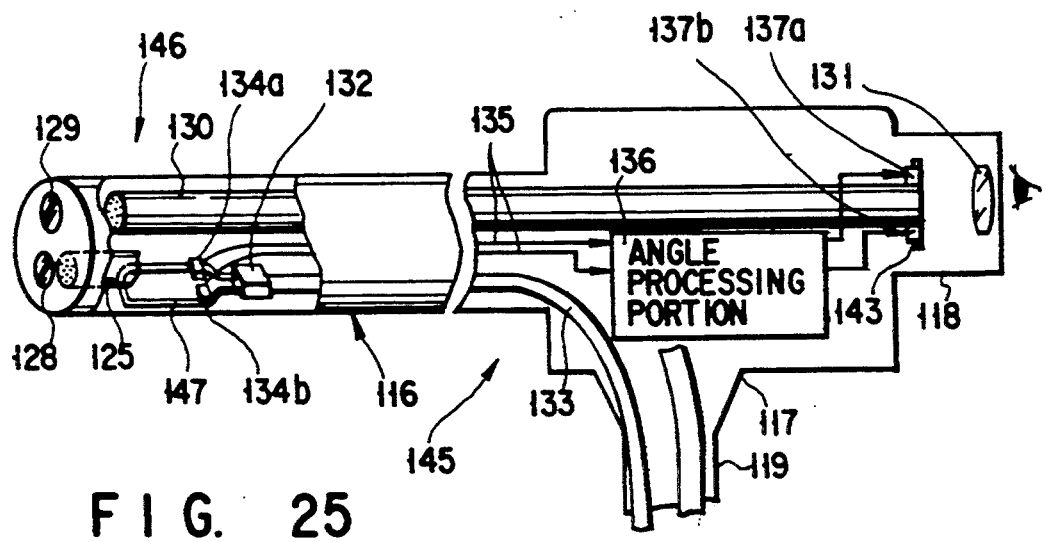
FIG. 25 is a general view showing the internal structure of an endoscope modified from the endoscope of FIG. 20.

A modification of the endoscope is shown at 145 in FIG. 25. In this modification, the printed substrate 111 is not used. A planar loop coil 147 is housed in the distal end portion 146, and the first and second magnetic detecting means 134a and 134b are arranged in the vicinity of the coil 147. The coil face of the coil 147 of this modification is parallel to the plane including the pivotal elements arranged horizontally as in the case of the first embodiment.

Figure 26:
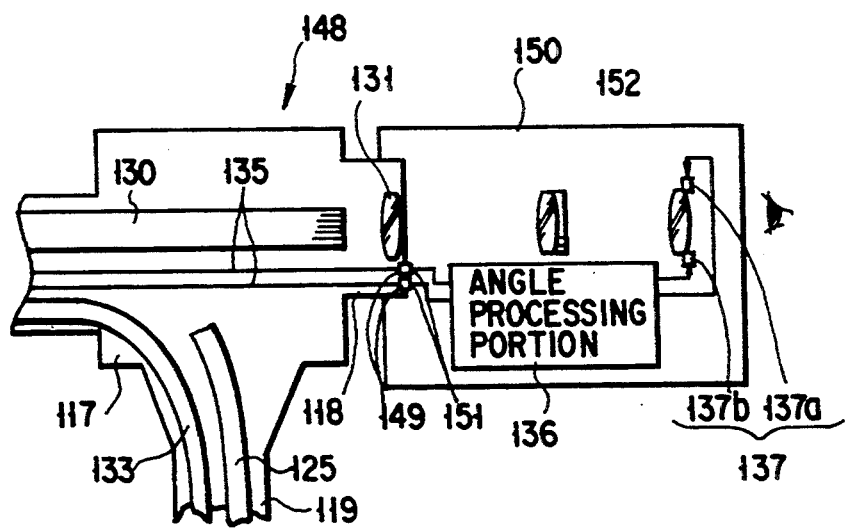
FIG. 26 is a general view showing the ocular portion of a further modified endoscope.

FIG. 26 shows a portion of the endoscope 148 which is at the side of the ocular portion. The endoscope 148 has signal lines 125 connected to contacts 149 provided on an end face of the ocular portion 118. An indicating adaptor 150 is detachably mounted on the ocular section 118. When the indicating adaptor 150 is mounted, the contacts 149 are connected to the angle processing portion 136 in the indicating adaptor 150 via contacts 151 provided at the side of the indicating adaptor 150.

The angle processing portion 136 is connected to the angle indicating portion 137 comprising the vertical angle indicating part 137a provided on the upper portion of an image optical system 152 in the indicating adaptor 150 and the horizontal angle indicating part 137b provided on the lower portion of the image optical system 152. The angle indicating portion 137 indicates the inclination angles of the bendable portion, as is in the embodiment shown in FIG. 24.

Figure 27:
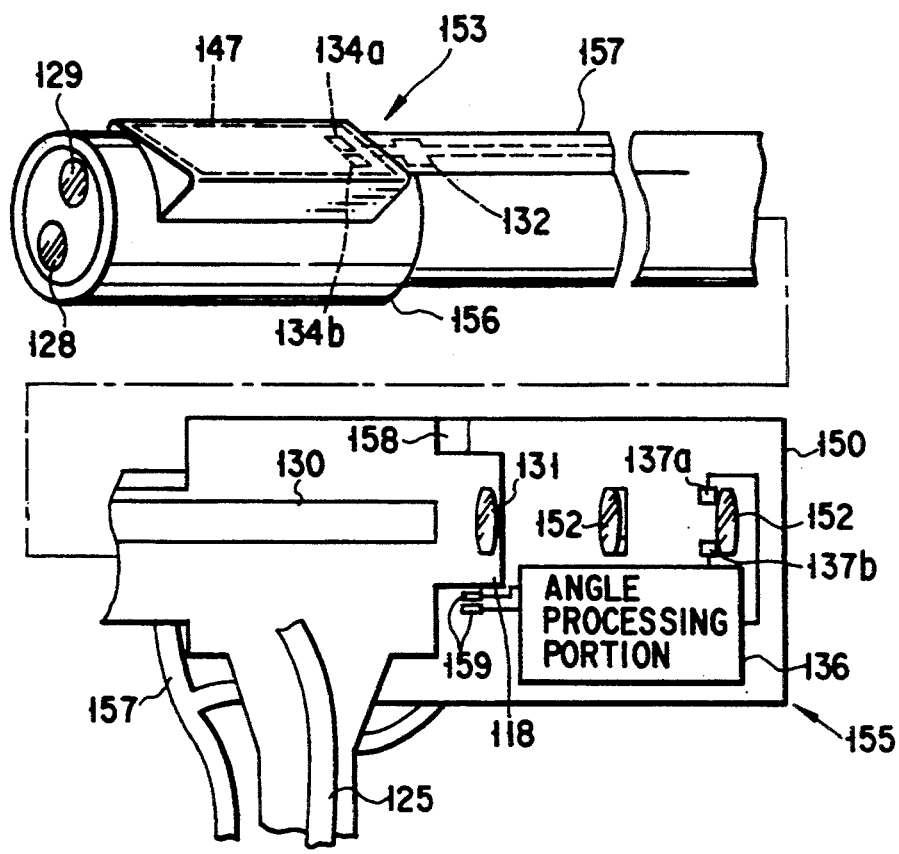
FIG. 27 is a general view of a still further modification of the endoscope of FIG. 20.
Figure 28:
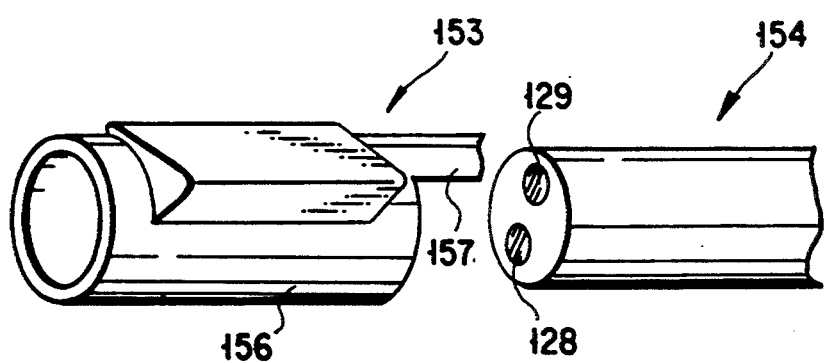
FIG. 28 is a perspective view of part of the endoscope of FIG. 27 in a state in which a probe is separated from the endoscope.

FIGS. 27 and 28 show a further embodiment of the endoscope apparatus shown at 155. The endoscope apparatus 155 comprises an ordinary endoscope 154, an MR probe or an MR adaptor 153 mounted on the endoscope 154 and an indicating adaptor 150 mounted on the ocular portion 118 of the endoscope 154. In FIG. 27, the endoscope apparatus 155 is shown in a state in which the MR probe 153 and the indicating adaptor 150 are mounted on the endoscope. In FIG. 28, on the other hand, the distal end portion of the MR probe 153 and the distal end portion of the endoscope 154 are shown in a separated state.

The endoscope 154 comprises a coil 147, first and second magnetic detecting means 134a and 134b, a matching circuit 132, a coaxial cable 133 and signal lines 135 all having the same structure as those of the endoscope 135 shown in FIG. 25 and provided in the MR probe 153. The angle processing portion 136 is housed in the indicating adaptor 150.

The MR probe 153 has a substantially cylindrical probe distal end portion 156 fitted on the distal end portion of the endoscope 154 and a cable portion 157 connected to the probe distal end portion 156. An coaxial cable and a signal line pass through the cable portion 157. One end of the signal line is connected to the branched cable portion 157, and the other end of the signal line is connected, through the contacts 159 of the ring 158 mounted on the ocular portion 118, to the angle processing portion 136 in the indicating adaptor 150. The coaxial cable is connected to a control device 114 similar to the control device 114 of FIG. 20. The other parts and elements are the same as those shown in FIG. 25 and 26.

This embodiment can use an ordinary endoscope which does not employ an MR signal receiving coil. However, it is necessary that at least the insertion section be made of non-ferromagnetic material.

Figure 29:
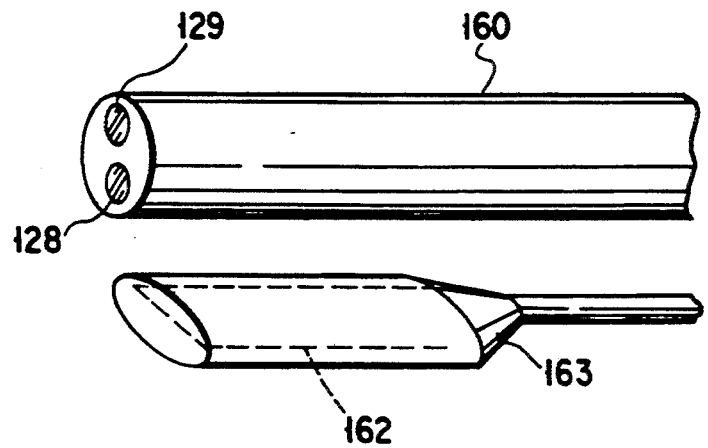
FIG. 29 is a general view of an endoscope, a part of which is modified from the endoscope of FIG. 27.

FIGS. 29 shows part of an endoscope modified from the endoscope shown in FIGS. 27 and 28. The endoscope 160 and the probe 163 in which the antenna 162 is housed are not unitarily formed but are separately provided. The portions of the endoscope 160 and the probe 163 at the operator side may be constructed similarly to those shown in FIG. 27 or may have another structure.

The magnetic detecting means may comprise a hall element, a magnetic reluctance element and another magnetic sensor.

In place of an endoscope provided with an image guide fiber bundle, an endoscope provided with a solid-state imaging device such as a CCD may be used. In this case, the angles detected by the magnetic detecting means may be indicated in the vicinity of the observation image by, for example, simultaneously indicating the angles together with the endoscope image on the monitoring image face, such that the angle of the coil face with respect to the static magnetic field during the observation of the endoscope image can be easily known.

Figure 30:
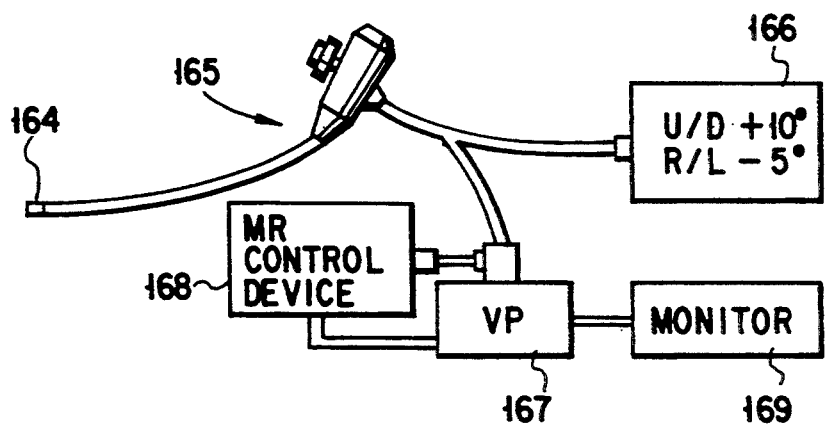
FIG. 30 is a general view of a still further modified endoscope and its peripheral appliances.

FIG. 30 shows an embodiment of an electronic endoscope 165 which has a distal end portion 164 housing a coil antenna and magnetic detecting means. An angle processing/indicating device 166 is connected to the electronic endoscope 165. With this device 166 the angles may be indicated in the similar manner as shown in FIG. 24, for example. The electronic endoscope 165 is connected to a video processor (hereinafter referred to the "VP") 167 in which are housed a signal processing portion for processing signals sent to the CCD and a light source portion for supplying illumination light. The electronic endoscope 165 is also connected to an MR control device 168 for producing MRI images sent to a signal line connected to the coil. The MR control device 168 is connected to the video processor 167 such that the MRI images are caused to overlap with each other to display them on the monitor 169.

Not only in the endoscope but also in the separate type MR probe, angle detecting and indicating means may be provided.

In the embodiments of FIGS. 20 to 24, driving means for driving the bending knob may be provided. The angle signals processed by the angle processing portion 136 are supplied to the angle indicating portion 137 and the driving means, and the driving means is driven by a coil setting switch or the like such that the angles indicated on the angle indicating portion 137 become zero. Parts of the above-mentioned embodiments and modifications can be combined.

As described above, each of the endoscopes shown in FIGS. 20 to 30 comprises an endoscope main body having an insertion section inserted in the body cavity of a living body, a signal receiving coil provided integrally with or separately from the endoscope main body for obtaining images due to a nuclear magnetic resonance imaging method, angle detecting means for detecting an angle between the face of the loop of the coil etc. and the static magnetic field and angle displaying means for indicating, in the vicinity of an endoscope observation image, the angle detected by the angle detecting means. As it can be known, in the vicinity of the endoscope observation image by means of the angle detecting means, whether the MRI images can be obtained easily, trial operation for checking whether the MRI images are obtained is not required.

Endoscope apparatuses shown in FIGS. 31 to 35 will be shown, with which cross sectional images of the portions from which information is to be collected can be obtained easily and MRI observation and diagnosis of the object portions can be simultaneously performed.

With the conventional MRI endoscope apparatus, NMR information on deep portions of tissues in a body cavity can be obtained easily. However, it takes a long time to obtain the cross sectional images of the object portions from which information is to be collected and thus the object portions cannot be diagnosed with ease. In other words, When MRI observation and diagnosis are performed, it takes a long time to obtain an image, and it is not easy to position the object portion at the diagnosing area, requiring repeated steps for doing so. Thus, a very long time is required for observation and diagnosis.

When the portions to be examined are observed optically and cross sectional images of the object portions due to MRI method are obtained, only the tissue surfaces can be observed. Thus, it is difficult to correlate the cross sectional images of the deep tissues with the observed tissue surfaces. In this case, it happens that it takes a long time to obtain the cross sectional images of the object portions from which information is to be collected.

Each of the endoscope apparatuses as shown in FIGS. 31 to 35 is invented to overcome these problems and is intended to observe and diagnose affected portions of the body cavity of a living body due to a nuclear magnetic resonance imaging (MRI) method. The endoscope apparatus is provided with an endoscope. The endoscope includes an insertion section having a distal end which houses an MR coil inserted in the body cavity, for sending and receiving high frequency signals and an ultrasonic oscillator for sending and receiving ultrasonic signals.

Observation is made by forming ultrasonic cross sectional images based on ultrasonic signals obtained by the ultrasonic oscillator provided in the distal end portion of the insertion of the endoscope, on one hand, and MRI observation and diagnosis are carried out due to high frequency signals detected by the MR coil, on the other hand.

Figure 31:
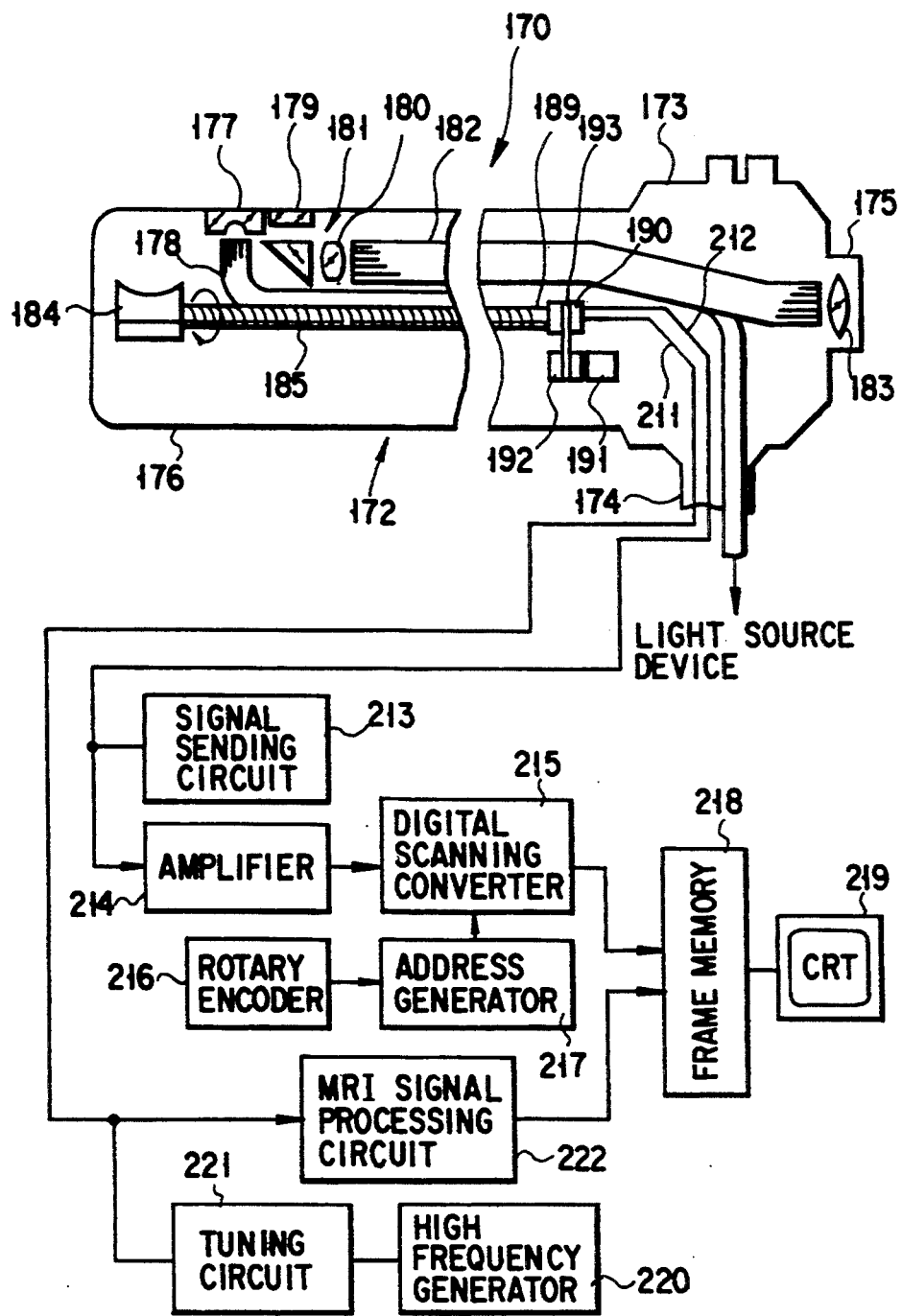
FIG. 31 is a general view showing the overall endoscope apparatus which is a further embodiment of this invention and facilitates instantaneous MRI observation and MRI diagnosis of an object to be examined.

As shown in FIGS. 31 and 32, the endoscope 170 comprises a elongated, flexible (for example) insertion section 172 and an thick operation section 173 provided on the rear end of the insertion section 172. A universal cord 174 extends from a lateral side of the operation section 173, and an ocular portion 175 is provided on the rear end portion of the operation section 173. An illumination window and an observation window are formed in a lateral side of the distal end portion 176 of the insertion section 172. The illumination window is provided with an orientation lens 177, to the rear end of which one end of a light guide fiber bundle 178 is connected. The light guide fiber bundle 178 extends through the insertion section 172, the operation section 173 and the universal cord 174 and its other end is connected to a light source device (not shown).

The observation window is provided with a cover glass 179 and an objective optical system 181 having an objective lens system 180 is disposed inside of the cover glass 179. The front end face of an image guide 182 comprising a fiber bundle is placed on the focal plane of the objective optical system 181. The image guide 182 extends through the insertion section 172 and the operation section 173 to the ocular part 175 such that the rear end of the image guide 182 faces an ocular lens or an eyepiece 183 provided in the ocular portion 175. The images of the object portion focused by the objective lens system 181 and transmitted through the image guide 182 can be observed at the ocular lens 175. An air supplying mechanism and a suction mechanism necessary for the endoscope are omitted in FIG. 31.

In the portion of the distal end portion at its distal end side is mounted an ultrasonic vibrating portion or probe 184, and a loop coil as an MR high-frequency coil for sending and receiving high frequency signals. The ultrasonic oscillating portion extends toward a lateral side of the distal end portion 176 and is rotated around the longitudinal axis of the insertion section 172 by means of a flexible shaft 185 rotatably extending through the insertion section 172.

As shown in FIG. 32, the main body of the distal end portion 176 comprises a rigid distal end portion 186 and an ultrasonic oscillator mounting member 187. The ultrasonic oscillating portion 184 which is rotatable is mounted in the ultrasonic oscillator mounting member 187. The front end of the flexible shaft 185 is connected to the shank portion 188 of the ultrasonic oscillating portion 184 extending through the rigid distal end portion 186. The flexible shaft 185 extends through the insertion section 172, and its other end portion projects into the operation section 173. To the rear end of the flexible shaft 185 is connected a driving shaft 189 to which a pulley 190, for example, is fixed (FIG. 31). In the operation section 173 is provided a motor 191 which is a rotational driving source, to the driving shaft of which a pulley 192 is fixed. A belt 193 is wound around the pulleys 190 and 192. As the motor 191 is rotated, the rotational force is transmitted through the flexible shaft 185 to rotate the ultrasonic oscillating portion 184.

As shown in FIG. 32, the ultrasonic oscillator mounting member 187 comprises a distal end portion and a cap-shaped short cylindrical body opened at its rear end face. The distal end part of the rigid distal end portion 186 has a ring-shaped distal end part closely fitted in the mounting member 187. Onto the outer peripheral stepped portion formed on the front end part of the rigid distal end portion 186 are closely fitted a spiral tube 194 and an outer sheath 195 covering the spiral tube 194. In the rigid distal end is provided an objective optical system 181 having the objective lens system 180. One end of the objective lens system 180 faces the inner face of the cover glass 179 exposed to the outer atmosphere and the other end of the objective lens system 180 faces the distal end face of the image guide 182.

The ultrasonic oscillating portion 184 in the mounting member 187 comprises an ultrasonic oscillator 198 fixedly received in an oscillator fixing member 196 by a receiving member 197, an acoustic lens 199 disposed on a wave sending and receiving surface of the ultrasonic oscillator 198, and a damping member 200 provided on the other surface of the ultrasonic vibrator 198. The oscillator fixing member 196 is a short cylindrical member with open upper and lower ends an is mounted in the mounting member 187 such that the axis of the member 196 is perpendicular to the axis of the insertion section. The open upper and lower ends of the oscillator fixing member 196 faces the peripheral surface of the mounting member 187. The pipe-shaped shank 188 extends perpendicularly to the central portion of the outer peripheral surface of the fixing member 196. The shank 188 forms a driving shaft for rotation-scanning the ultrasonic vibrator 198 and extends from the central opening 186a on the annular front end of the rigid distal end portion 186 to the interior thereof.

In an outside portion from the center of the oscillator fixing member 196, the ultrasonic oscillator 198 is disposed horizontally with its wave sending and receiving surface being directed toward the open upper end of the member 196 and is fixed thereto by the receiving member 197. The acoustic lens 199 also used as a matching layer is fixed to the wave sending and receiving surface of the ultrasonic oscillator 198. At the opposite side of the ultrasonic oscillator 198 to the wave sending and receiving surface is provided the damping member 200 in the receiving member 197. The shank 188 extending into the rigid distal end portion 186 is rotatably supported by a bearing member 201 such as a bearing fixed to the rigid distal end portion 186. The outer peripheral surface of the rear end portion of the shank 188 is stepped to form a small diameter portion 188a on which the front end portion of the flexible shaft 185 comprising an electrically conductive wire closely wound in a coil form is mounted. The flexible shaft 185 may be a double-layered coil. Fixedly screwed to the rigid end portion 186 is a fixing member 202 for integrally connecting the bearing member 201 to the rigid distal end portion 186. A guide tube 203 covering the flexible shaft 185 is tightened to the fixing member 202 by a nut 204. Through the flexible shaft 185 extends a lead line 205 for sending driving pulse signals to the ultrasonic oscillator 198 and sending receiving signals of the oscillator 198 to an external amplifier. The lead line 205 comprises an electric wire 205a covered with an electrically insulating film. The lead line 205 extends through the pipe-shaped shank 188. The electric wire 205a is connected to a terminal of the signal line of the ultrasonic oscillator 198 within the oscillator fixing member 196 and is used as a signal transmitting line. The earth terminal of the ultrasonic oscillator 198 is connected to the oscillator fixing member 196 by a lead line 206 passing through the opening of the receiving member 197. The lead lines 205 and 206, and the flexible shaft 205 electrically connected to the lead line 206 via the electrically conductive shank 188 form a coaxial cable of a conventional type.

The interior of the ultrasonic oscillator mounting member 187 and the interior of the guide tube 203 communicating with the interior of the mounting member 187 via the opening 186a and the bearing member 201 are filled with an ultrasonic wave transmitting medium 207 for reducing friction of the flexible shaft 185 and the guide tube 203. In the outer peripheral surface of the thick front end portion of the mounting member 187 and the outer peripheral surface of the front end portion of the rigid distal end portion 186 are respectively formed V grooves 208 and 209 to which a balloon is provided for acoustically, closely contacting the ultrasonic transmitting portion to the wall of a body cavity so as not to form an air gap therebetween. An air supplying port and an air supplying passage which are necessary for expanding the balloon are not shown in FIG. 32.

In the ultrasonic oscillator mounting member 187 is provided a rectangular loop antenna 210 extending along the inner peripheral surface of the member 187. In this embodiment, the loop antenna 210 is fixedly mounted in the ultrasonic oscillator mounting member 187. A signal line 211 for transmitting high frequency signals extends through the rigid distal end portion 186 and the insertion section 172 and is connected to the loop antenna 210 via a matching circuit (not shown). The signal line 211 further extends through the universal cord 174 and is connected to an MRI device. A signal line 212 extends through the insertion section 172 and the universal cord 174 and is connected to the ultrasonic vibrating portion 184 via the lead lines 205 and 206 and an ultrasonic observation device.

As shown in FIG. 31, the ultrasonic observation device comprises a signal generating circuit 213, an amplifier 214, a digital scanning converter 215, a rotary encoder 216 and an address generator 217. The signal line 212 is connected to the amplifier 214 via the signal sending circuit 213. The output terminal of the amplifier 214 is connected to the digital scanning converter 215. The ultrasonic signals from the signal sending circuit 213 are sent out by the ultrasonic oscillator 198, and the reflected wave signals received by the ultrasonic oscillator 198 from the object portion are input to the digital scanning converter 215 via the amplifier 214. The output terminal of the digital scanning converter 215 is connected to the a CRT monitor 219 via a frame memory 218. The address generator 217 is connected to the rotary encoder 216. To the digital converter 215 is supplied a data of ultrasonic cross sectional images (for example, ultrasonic B mode image data) obtained from coordinate signals given by the rotary encoder 216 and the address generator 217 based on the output signals from the ultrasonic oscillator 198. The signals of the digital scanning converter 215 are supplied to the frame memory 218.

The MRI device comprises a high frequency generator 220, a tuning circuit 221 and an MRI signal processing circuit 222. The high frequency generator 220 is connected to the tuning circuit 221 to which the MRI signal processing circuit 222 is connected. High frequency signals generated by the high frequency generator 220 are tuned in the tuning circuit 221 at a resonance frequency corresponding to the frequency of the object portion and sent out from the loop coil 210 (FIG. 32). MR signals from the object portion received by the loop coil 210 are supplied to the MRI signal processing circuit 222. Information on MR signals at relaxation time or the like (MR parameters) are detected to be formed as MR cross sectional images. The output signals of the digital scanning converter 215 and the output signals of the MRI signal processing circuit 222 are stored in the frame memory 218, and MRI cross sectional images and the ultrasonic cross sectional images are displayed on the CRT monitor 219.

The operation of the endoscope apparatus shown in FIGS. 31 and 32 will be described.

The endoscope apparatus of this embodiment has a permanent magnet, a normal conductive magnet, and a super conductive magnet or the like and is used together with static magnetic field generating means. A static magnetic field is generated by the static magnetic field generating means, and the endoscope 170 is inserted in the object portion of the body cavity of a person to be examined or a patient placed in the static magnetic field, by observing, at the ocular portion, the optical images formed by the observation optical system such as the objective lens system.

Upon diagnosis, the static magnetic field is first applied to the patient by means of the static magnetic field generating means. High frequency signals are sent from the loop coil 210 to the object portion and received by the former from the latter. Then, NMR parameters based on the MR signals from the object portion are detected by means of the MRI device and the MRI images are formed.

In this embodiment, ultrasonic diagnosis is performed by sending and receiving the ultrasonic signals by the ultrasonic oscillator 198 in the distal end portion of the insertion section, prior to MRI diagnosis. More specifically, an object portion or an affected portion of a person to be examined or a patient in which the examiner is interested is examined under the observation of the ultrasonic cross sectional images. By moving the insertion section 172 of the endoscope 170, the ultrasonic vibrator 198 and the loop coil 210 are set at such positions at which the cross sectional image of the object portion is obtained properly.

The MR endoscope 170 uses a radial mechanical scanning method for rotating the ultrasonic vibrator 198 mechanically. Signal sending pulses are sent to the ultrasonic vibrator 198 and drives the same and ultrasonic pulses are emitted to the object portion in the body cavity of the living body. The ultrasonic pulses are reflected at the boundaries of the tissues of the living body and return to the ultrasonic vibrator 198 as echoes and are converted into telegraph signals. The telegraph signals are input to the digital scanning converter 215 of the ultrasonic observation device to be formed into data of ultrasonic cross sectional images. The outputs from the digital scanning converter 215 are supplied to the monitor 219 via the frame memory 218 and indicated as ultrasonic cross sectional images on the monitor 219.

The endoscope of this embodiment is of a lateral viewing type for purposes of the optical observation and the ultrasonic observation. MR signals detected by the loop coil 210 are observed at the lateral side of the endoscope. In this regard, the ultrasonic cross sectional image obtained by the ultrasonic vibrator 198 at least partially overlaps with the MRI cross sectional image. Thus, the loop coil 210 can be placed at such a position that the object portion to be examined is located at the MR diagnosis area by placing the distal end portion 176 of the MR endoscope 170 so as to obtain an ultrasonic cross sectional image of the object portion to be examined.

After the object portion to be examined has been specified and the loop coil 210 has been placed in such a position that the object position has been positioned in the MRI diagnosing area, the MRI cross sectional image is formed and diagnosis is performed. In other words, high frequency signals generated by the high frequency generator 220 are supplied by the loop coil 210 to the object portion in the body cavity via the tuning circuit 221. The MR signals are received by the loop coil 210 and the NMR parameters are detected by the MRI signal processing circuit 222 in the MRI device, whereby the MRI cross sectional image is formed. The outputs of the MRI signal processing circuit 222 are input to the monitor 219 via the frame memory 218, and the MRI cross sectional image is shown in the monitor 219. Alternatively, the ultrasonic cross sectional image and the MRI cross sectional image may be combined by the frame memory and the combined image may be displayed on the monitor 219.

As described above, the ultrasonic vibrator and the loop coil are provided in the distal end portion of the endoscope so as to perform both ultrasonic diagnosis and MRI diagnosis. With this structure, the loop coil can be placed in such a position that the object portion is positioned in the diagnosing area, enabling the object portion to be examined easily and accurately due to the MRI diagnosis, whereby MRI observation and diagnosis can be performed simultaneously.

FIGS. 33 and 34 show a modified arrangement of the loop coil in the distal end portion of the insertion section of the NR endoscope.

The endoscope as shown in FIG. 33 has an elongated insertion section similar to the endoscope shown in FIGS. 31 and 32. The distal end portion 230 of the insertion section comprises a rigid distal end portion 186 and an ultrasonic vibrator mounting member 187. An ultrasonic oscillating potion 184 is rotatably mounted in the ultrasonic vibrating portion 184 provided with an ultrasonic vibrator 198. The ultrasonic vibrating portion 184 is soaked in an ultrasonic wave transmitting medium 207.

On the opposite surface of the ultrasonic vibrator 198 to the wave sending and receiving surface is provided a circular loop coil 231 so as to be rotatable together with the ultrasonic vibrator 198, as shown in FIG. 34. The ultrasonic oscillator 198 and the flexible shaft 185 are connected to an ultrasonic observation device and an MRI device similar to those shown in FIG. 31 by signal lines 212 and 211 extending through the shank 188 and the flexible shaft 185.

The other parts and elements are the same as those of the endoscope apparatus shown in FIGS. 31 and 32, and their description is omitted.

Like the endoscope shown in FIGS. 31 and 32, the endoscope of this embodiment is used to produce ultrasonic cross sectional images by sending and receiving ultrasonic waves and the reflected waves from the tissues in the body cavity as to specify the to-be-examined portion in the body cavity. With this embodiment, the to-be-examined object portion is placed in the MRI diagnosing area due to the loop antenna 231 by moving the ultrasonic vibrating portion 184 to a position at which the accurate ultrasonic cross sectional image of the object portion can be obtained. After the object portion has been specified and then the loop coil 231 has been set in a position at which the object portion is in the MRI diagnosing area, the MRI diagnosis is performed. That is, high frequency signals are sent from and received by the loop coil 231, the NMR parameters based on the MR signals from the object portion are detected by the MRI device, and diagnosis is performed by checking the obtained MRI cross sectional images.

In the embodiment shown in FIGS. 31 and 32, the loop coil is fixed to the ultrasonic vibrator mounting member. In this embodiment, however, the loop coil 231 is provided on the ultrasonic oscillating portion 184 so as to be rotatable together with the ultrasonic vibrator 198. Thus, the positional relation between the ultrasonic cross sectional images obtained by the ultrasonic vibrator 198 and the MRI cross sectional images obtained by the loop coil 231 can be clearly known. This makes it very easy to obtain the cross sectional images of the object portion, the information on which is required.

FIG. 35 is a longitudinal cross sectional view of the ultrasonic vibrator showing another modified arrangement of the loop coil.

The ultrasonic vibrating portion 240 provided in the ultrasonic vibrator mounting member according to this modification comprises an ultrasonic vibrator 198 and a loop coil 241. The loop coil 241 surrounds the outer peripheral wall of the wave sending and receiving surface of the ultrasonic vibrating portion 240 and is rotatable therewith. The ultrasonic vibrator 198 is connected to the ultrasonic observation device by the signal line 212, and the loop coil 241 is connected to the MRI device by the signal line 211. The other structure is the same as the embodiment shown in FIGS. 33 and 34.

Similarly to the embodiment shown in FIGS. 33 and 34, with this embodiment having the loop coil arranged at the side of the wave sending and receiving surface of the ultrasonic vibrating portion, the positional relation between the ultrasonic cross sectional images obtained by the ultrasonic vibrator 198 and the MRI cross sectional images obtained by the loop coil 241 is known clearly. Thus, the cross sectional images of the object portion can be obtained more easily, and MRI observation and diagnosis can be performed simultaneously.

With the endoscope apparatuses as shown in FIGS. 31 to 35, the cross sectional images of the object portion can be obtained more easily, and MRI observation and diagnosis can be performed simultaneously.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An apparatus for receiving nuclear-magnetic resonance signals produced by applying a high frequency energy to a living body disposed in a static magnetic field in use with an MRI system, which comprises:
   an elongated insertion member having a distal end portion adapted to be inserted in a body cavity of said living body, a proximal end portion adapted to be provided externally of said living body, a rigid portion provided on said distal end portion and having an axis, and a bendable portion provided between said proximal end portion and said distal end portion;
   operating means extending through said insertion member and operated at said proximal end portion so as to bend said bendable portion to move said rigid portion transversely of said axis thereof; and
   receiving means provided between said rigid portion and said bendable portion, for receiving nuclear-magnetic resonance signals, said receiving means including:
   a casing having axially extending end portions and provided between said rigid portion and said bendable portion; and
   a high frequency coil situated in said casing.

2. The apparatus according to claim 1, wherein said high frequency coil is provided with an opening having a central axis extending transversely of said axis of said rigid portion.

3. The apparatus according to claim 2, wherein said casing has an axis aligned with said axis of said rigid portion and can be moved together with said rigid portion transversely of said axis of said casing with said axes of said casing and said rigid portion kept aligned with each other.

4. The apparatus according to claim 1, wherein said casing has a cylindrical inner surface and said high frequency coil has a flexible sheet-shaped substrate made of electrically insulating material and fixed to said cylindrical inner surface of said casing, and a high frequency coil element printed on said substrate.

5. The apparatus according to claim 4, wherein said high frequency coil is provided with a central opening having a major axis substantially parallel to said axis of said rigid portion and a minor axis perpendicular to said major axis having substantially half a circumferential length of said casing.

6. The apparatus according to claim 5, wherein said central opening of said high frequency coil has a substantially rectangular shape.

7. The apparatus according to claim 5, further comprising a matching circuit housed in said casing and connected to said high frequency coil element, and a high frequency signal line having an end connected to said matching circuit.

8. The apparatus according to claim 4, further comprising bonding means for bonding said substrate to said cylindrical inner surface of said casing.

9. The apparatus according to claim 4, further comprising a semi-cylindrical fixing member provided in said casing, for fixing said substrate to said inner surface of said casing with said substrate held between said fixing member and said casing.

10. The apparatus according to claim 9, wherein said rigid portion has a rigid main body, and said fixing member has an end connected to said main body.

11. The apparatus according to claim 10, wherein said main body has a groove receiving said one end of said fixing member.

12. The apparatus according to claim 11, wherein said main body comprises:
   a small diameter portion housed in an axially extending end portion of said casing; and
   an intermediate diameter portion having an end face to which end face said axially extending end portion of said casing is abutted and said groove is opened.

13. The apparatus according to claim 9, which further comprises:
   a matching circuit housed in said casing and connected to said high frequency coil element; and
   a signal line extending toward said proximal end portion of said insertion member in said insertion member and having one end connected to said matching circuit; and
   wherein said fixing member comprises an assembling portion having a pair of supporting arms arranged for circumferentially positioning at least one element of said matching circuits, said supporting arms protruding from said fixing member and toward said proximal end portion of said insertion member.

14. The apparatus according to claim 13, wherein said high frequency coil element is provided with a central opening having a major axis substantially parallel to said axis of said rigid portion and a minor axis perpendicular to said major axis, and said casing has a cylindrical outer peripheral surface and marks formed on the outer peripheral surface, for indicating a position of said high frequency coil.

15. The apparatus according to claim 13, further comprising a high frequency signal line extending through said insertion section to said proximal end thereof and a fixing member to which said high frequency signal line is connected.

16. The apparatus according to claim 1, wherein said insertion member comprises an endoscope.

17. The apparatus according to claim 16, wherein said endoscope comprises an objective lens system provided in said rigid portion, observation means having an observation view field for observing an image focused by said objective lens system, and means for providing information on a position of said high frequency coil.

18. The apparatus according to claim 17, wherein said high frequency coil includes an opening with a central axis perpendicular to said axis of said rigid portion, and said means for providing information includes a mark for indicating a direction of said central axis of said opening of said high frequency coil.

19. The apparatus according to claim 18, wherein said information includes marks indicating planes including said opening of said coil.

20. The apparatus according to claim 19, wherein said marks include cut-outs in said observation visual field.

21. The apparatus according to claim 19, wherein said marks includes projections projecting outward of said visual field.

22. The apparatus according to claim 21, wherein said endoscope is an electronic endoscope having a monitoring device for displaying said marks.

23. The apparatus according to claim 17, wherein said endoscope has means for providing information on bending direction of said bendable portion.

24. The apparatus according to claim 17, wherein said rigid portion has a forceps outlet for inserting forceps in said body cavity and said endoscope has a channel tube extending through said insertion section and a pipe made of non-ferromagnetic metal axially separated from said high frequency coil and causing said forceps outlet to communicate with said channel tube.

* * * * *